United States Patent
Klein et al.

(10) Patent No.: US 10,730,976 B2
(45) Date of Patent: Aug. 4, 2020

(54) LIPID ANALOGS AND LIPOSOMES COMPRISING SAME

(71) Applicant: Yeda Research and Development Co. Ltd., Rehovot (IL)

(72) Inventors: Jacob Klein, Rehovot (IL); Weifeng Lin, Rehovot (IL); Ronit Goldberg, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 16/064,498

(22) PCT Filed: Dec. 22, 2016

(86) PCT No.: PCT/IL2016/051372
§ 371 (c)(1),
(2) Date: Jun. 21, 2018

(87) PCT Pub. No.: WO2017/109784
PCT Pub. Date: Jun. 29, 2017

(65) Prior Publication Data
US 2019/0002609 A1  Jan. 3, 2019

(30) Foreign Application Priority Data

Dec. 22, 2015  (IL) .......................................... 243285

(51) Int. Cl.
| | | |
|---|---|---|
| C07F 9/10 | (2006.01) | |
| C08F 130/02 | (2006.01) | |
| A61K 9/127 | (2006.01) | |
| A61K 9/08 | (2006.01) | |
| A61P 19/02 | (2006.01) | |
| A61K 9/00 | (2006.01) | |
| A61K 47/69 | (2017.01) | |

(52) U.S. Cl.
CPC .......... *C08F 130/02* (2013.01); *A61K 9/0051* (2013.01); *A61K 9/08* (2013.01); *A61K 9/1273* (2013.01); *A61P 19/02* (2018.01); *C07F 9/106* (2013.01); *A61K 9/0019* (2013.01); *A61K 47/6909* (2017.08); *C08F 2438/01* (2013.01)

(58) Field of Classification Search
None
See application file for complete search history.

(56) References Cited

U.S. PATENT DOCUMENTS 8,617,592 B2   12/2013   Jiang et al.
8,765,432 B2    7/2014   Charles et al.

FOREIGN PATENT DOCUMENTS

| CN | 102351984 | * 12/2013 | ............ C08F 220/36 |
|---|---|---|---|
| EP | 0032622 | 7/1981 | |
| EP | 0251229 | 1/1988 | |
| JP | 61-129192 | 6/1986 | |
| JP | 61-155392 | 7/1986 | |
| JP | 07-010874 | 2/1995 | |
| WO | WO 2004/062596 | 7/2004 | |
| WO | WO 2011/158237 | 12/2011 | |
| WO | WO 2015/001564 | 1/2015 | |
| WO | WO 2015/193887 | 12/2015 | |
| WO | WO 2015/193888 | 12/2015 | |
| WO | WO 2017/109784 | 6/2017 | |

OTHER PUBLICATIONS

Morigaki et al., Angew. Chem. Int. Ed., 2001, 40(1), pp. 172-174. (Year: 2001).*
Yamamoto et al. J.Oleo Sci., 2006, 55(9), pp. 465-471 (Year: 2006).*
Seo et al., Macromol. Reports, 1995, A32(S7), pp. 999-1006. (Year: 1999).*
Communication Pursuant to Article 94(3) EPC dated May 7, 2019 From the European Patent Office Re. Application No. 16831643.8. (4 Pages).
International Preliminary Report on Patentability dated Apr. 28, 2017 From the International Bureau of WIPO Re. Application No. PCT/IL2016/051372. (14 Pages).
International Search Report and the Written Opinion dated Apr. 28, 2017 From the International Searching Authority Re. Application No. PCT/IL2016/051372. (14 Pages).
Office Action dated Jul. 3, 2016 From the Israel Patent Office Re. Application No. 243285.
Office Action dated May 30, 2016 From the Israel Patent Office Re. Application No. 243285.

(Continued)

*Primary Examiner* — Brian Gulledge

(57) ABSTRACT

A polymeric compound is disclosed herein, having the general formula I:

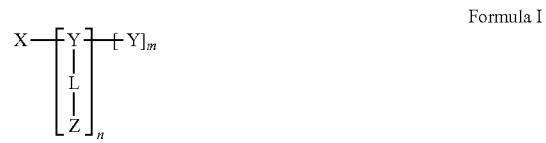

Formula I wherein m, n, X, Y, Z and L are as defined herein. Further disclosed herein are lipid bilayers comprising at least one bilayer-forming lipid and the aforementioned polymeric compound, and liposomes comprising such a bilayer, as well as methods, uses and compositions utilizing such bilayers and/or liposomes for reducing a friction coefficient of a surface and/or for inhibiting biofilm formation.

20 Claims, 10 Drawing Sheets
(9 of 10 Drawing Sheet(s) Filed in Color)
Specification includes a Sequence Listing.

(56) References Cited

OTHER PUBLICATIONS

Chen et al. "Lubrication at Physiological Pressures by Polyzwitterionic Brushes", Science, XP055364700, 323(5922): 1698-1701, Mar. 27, 2009.
Dong et al. "Distribution and Inhibition of Liposomes on *Staphylococcus aureus* and Pseudomonas aeruginosa Biofilm", PLOS ONE, 10(6): e0131806-1-e0131806-16, Jun. 30, 2015.
Goldberg et al. "Boundary Lubricants With Exceptionally Low Friction Coefficients Based on 2D Close-Packed Phosphatidylcholine Liposomes", Advanced Materials, 23(31): 3517-3521, Published Online Jul. 4, 2011.
Goldberg et al. "Interactions Between Adsorbed Hydrogenated Soy Phosphatidylcholine (HSPC) Vesicles at Physiologically High Pressures and Salt Concentrations", Biophysical Journal, 100(10): 2403-2411, May 2011.
Goldberg et al. "Liposomes as Lubricants: Beyond Drug Delivery", Chemistry and Physics of Lipids, 165(4): 374-381, Available Online Nov. 19, 2011.
Harris et al. "Effect of Pegylation on Pharmaceuticals", Nature Reviews Drug Discovery, 2(3): 214-221, Mar. 2003.
Kusumi et al. "Dynamic and Structural Properties of Polymerized Phosphatidylcholine Vesicle Membranes", Journal of the American Chemical Society, XP055038340, 105(10): 2975-2980, May 1, 1983. Fig.1.
Moghimi et al. "Stealth Liposomes and Long Circulating Nanoparticles: Critical Issues in Pharmacokinetics, Opsonization and Protein-Binding Properties", Progress in Lipid Research, 42(6): 463-478, Nov. 2003.
Morigaki et al. "Patterning Solid-Supported Lipid Bilayer Membranes by Lithographic Polymerization of a Diacetylene Lipid", Angewandte Chemie International Edition, XP001006346, 40(1): 172-174, Jan. 2001. Fig. Scheme 1.
Singh et al. "Polymerizable Phospholipids: A Novel Class of Biomaterials", Polymers for Advanced Technologies, XP000454792, 5(7): 358-373, Jul. 5, 1994. Fig. 1, Schemes 1-3.
Sorkin et al. "Origins of Extreme Boundary Lubrication by Phosphatidylcholine Liposomes", Biomaterials, 34(22): 5465-5475, Available Online Apr. 23, 2013.

\* cited by examiner

LIPID ANALOGS AND LIPOSOMES COMPRISING SAME

RELATED APPLICATIONS

This application is a National Phase of PCT Patent Application No. PCT/IL2016/051372 having International filing date of Dec. 22, 2016, which claims the benefit of priority of Israel Patent Application No. 243285 filed on Dec. 22, 2015. The contents of the above applications are all incorporated by reference as if fully set forth herein in their entirety.

SEQUENCE LISTING STATEMENT

The ASCII file, entitled 74172SequenceListing.txt, created on Jun. 21, 2018, comprising 734 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to material science and, more particularly, but not exclusively, to novel polymeric compounds usable, inter alia, for forming liposomes.

Phosphatidylcholine (PC) liposomes at surfaces are known to be extremely good lubricants, even at high pressures [Goldberg et al., Adv Materials 2011, 23:3517-3521; Goldberg et al., Biophys J 2011, 100:2403-2411; Sorkin et al., Biomaterials 2014, 34:5465-5475].

Aggregation of liposomes into macroscopic aggregates can interfere with the use of liposomes in different ways. Large aggregates can precipitate and sediment out of a dispersion, rendering the dispersion unusable; aggregates larger than about 200-300 nm scatter visible light, leading to turbidity, which may interfere with a use of liposomes in which transparency is important; and furthermore, large aggregates injected into the body are more prone to protein adsorption, and to attack and removal by macrophages [Moghimi & Szebeni, Prog Lipid Res 2003, 42:463-478].

PEGylated PC small unilamellar vesicles (SUVs) have been used for drug delivery, wherein PEG brushes are incorporated in the membrane bilayer; these brushes extend out from the SUV surfaces and sterically-stabilize them against aggregation [Harris & Chess, Nat Rev Drug Discov 2003, 2:214-221]. However, PEGylation was reported to reduce the efficiency of SUVs for lubrication purposes at high pressures (such as in joints), as the PEG chains are not highly hydrated and do not in themselves form good lubricants at high pressures [Goldberg et al., Adv Materials 2011, 23:3517-3521].

U.S. Pat. No. 8,617,592 describes block copolymers and conjugates comprising a zwitterionic poly(carboxybetaine), poly(sulfobetaine) or poly(phosphobetaine) block, and a hydrophobic block, which self-assemble into particles, and the use of such particles for delivering therapeutic and diagnostic agents.

Chen et al. [Science 2009, 323:1698-1702] describes effective lubrication by poly[2-(methacryloyloxy)ethyl phosphorylcholine] (PMPC) brushes, and attributes this phenomenon to strong hydration of the zwitterionic monomers.

Additional background art includes Goldberg & Klein [Chem Phys Lipids 2012, 165:374-381]; International Patent Application Nos. PCT/IL2014/050604 (published as WO 2015/001564), PCT/IL2015/050605 and PCT/IL2015/050606; and Israel Patent Application No. 234929.

SUMMARY OF THE INVENTION

According to an aspect of some embodiments of the invention, there is provided a polymeric compound having the general formula I:

Formula I wherein:
m is zero or a positive integer;
n is an integer which is at least 1, wherein when X does not comprise a phosphate group, n is at least 2;
X is a lipid moiety;
Y is a backbone unit which forms a polymeric backbone;
L is absent or is a linking moiety; and
Z has the general formula II:

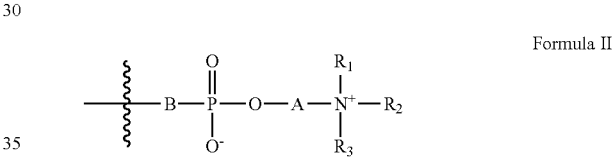

Formula II wherein:
A is a substituted or unsubstituted hydrocarbon;
B is an oxygen atom or is absent; and
$R_1$-$R_3$ are each independently selected from the group consisting of hydrogen, alkyl, cycloalkyl, heteroalicyclic, aryl and heteroaryl.

According to an aspect of some embodiments of the invention, there is provided a lipid bilayer comprising at least one bilayer-forming lipid and the polymeric compound according to any of the respective embodiments described herein.

According to an aspect of some embodiments of the invention, there is provided a liposome comprising at least one lipid bilayer according to any of the respective embodiments described herein.

According to an aspect of some embodiments of the invention, there is provided a lubricant composition comprising liposomes according to any of the respective embodiments described herein and a carrier.

According to an aspect of some embodiments of the invention, there is provided a method of reducing a friction coefficient of a surface, the method comprising contacting the surface with liposomes according to any of the respective embodiments described herein.

According to an aspect of some embodiments of the invention, there is provided a use of a liposome of according to any of the respective embodiments described herein in the manufacture of a medicament for treating a synovial joint disorder associated with an increased friction coefficient of an articular surface in the synovial joint.

According to an aspect of some embodiments of the invention, there is provided a method of inhibiting biofilm formation on a surface of a substrate, the method comprising contacting the substrate with a composition which comprises liposomes to any of the respective embodiments described herein.

According to an aspect of some embodiments of the invention, there is provided an article of manufacture comprising a composition-of-matter, the composition-of-matter comprising a substrate coated, on at least a portion of a surface thereof, by a lipid bilayer according to any of the respective embodiments described herein.

According to some embodiments of the invention, Y is a substituted or unsubstituted alkylene unit.

According to some embodiments of the invention, Y is a substituted or unsubstituted ethylene unit.

According to some embodiments of the invention, Y has the formula —$CR_4R_5$—$CR_6D$-, wherein:

when Y is a backbone unit which is not attached to L or Z, D is $R_7$; and when Y is a backbone unit which is attached to L or Z, D is a covalent bond or a linking group attaching Y to L or Z, the linking group being selected from the group consisting of —O—, —S—, alkylene, arylene, sulfinyl, sulfonyl, phosphate, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino; and $R_4$-$R_7$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, azo, phosphate, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino.

According to some embodiments of the invention, $R_4$ and $R_5$ are each hydrogen.

According to some embodiments of the invention, $R_6$ is hydrogen.

According to some embodiments of the invention, the linking group is selected from the group consisting of —O—, —C(=O)O—, —C(=O)NH— and phenylene.

According to some embodiments of the invention, the linking group is —C(=O)O—.

According to some embodiments of the invention, L is a substituted or unsubstituted hydrocarbon from 1 to 10 carbon atoms in length.

According to some embodiments of the invention, L is a substituted or unsubstituted ethylene group.

According to some embodiments of the invention, B is an oxygen atom.

According to some embodiments of the invention, A is a substituted or unsubstituted hydrocarbon from 1 to 4 carbon atoms in length.

According to some embodiments of the invention, A is a substituted or unsubstituted ethylene group.

According to some embodiments of the invention, $R_1$-$R_3$ are each independently hydrogen or $C_{1-4}$-alkyl.

According to some embodiments of the invention, $R_1$-$R_3$ are each methyl.

According to some embodiments of the invention, n is at least 3.

According to some embodiments of the invention, n is in a range of from 3 to 1,000, and m is in a range of from 0 to 1,000.

According to some embodiments of the invention, n is in a range of from 5 to 50, and m is in a range of from 0 to 50.

According to some embodiments of the invention, at least a portion of Y, L and/or Z comprise at least one targeting moiety.

According to some embodiments of the invention, the polymeric compound has the general formula Ib:

$$X-\left[\begin{array}{c}Y\\|\\L\\|\\Z\end{array}\right]_n-(Y)_{m-1}-T \qquad \text{Formula Ib}$$

wherein:

T is a unit of Y which comprises at least one targeting moiety, as described hereinabove;

X and T are attached to distal termini of the polymeric compound; and

X, Y, L, Z, n and m are as defined for general formula I, with the proviso that m is a positive integer.

According to some embodiments of the invention, the lipid is selected from the group consisting of a fatty acid, a monoglyceride, a diglyceride, a triglyceride, a glycerophospholipid, a sphingolipid, and a sterol.

According to some embodiments of the invention, the glycerophospholipid is selected from the group consisting of a phosphatidyl ethanolamine, a phosphatidyl serine, a phosphatidyl glycerol and a phosphatidyl inositol.

According to some embodiments of the invention, X has the general formula III:

$$\begin{array}{c}W_1-O\\W_2-O\\\phantom{W_2-}O-J-K-M-Q-\end{array} \qquad \text{Formula III}$$

wherein:

$W_1$ and $W_2$ are each independently selected from the group consisting of hydrogen, alkyl, alkenyl, alkynyl and acyl, wherein at least one of $W_1$ and $W_2$ is not hydrogen;

J is —P(=O)(OH)—O— or absent;

K is a substituted or unsubstituted hydrocarbon from 1 to 10 carbon atoms in length;

M is a linking group selected from the group consisting of —O—, —S—, amino, sulfinyl, sulfonyl, phosphate, phosphonyl, phosphinyl, carbonyl, thiocarbonyl, urea, thiourea, carbamyl, thiocarbamyl, amido, carboxy, and sulfonamide, or absent; and Q is a substituted or unsubstituted hydrocarbon from 1 to 10 carbon atoms in length, or absent, wherein when M is absent, Q is also absent.

According to some embodiments of the invention, J is —P(=O)(OH)—O— and K is selected from the group consisting of an ethanolamine moiety, a serine moiety, a glycerol moiety and an inositol moiety.

According to some embodiments of the invention, M is amido.

According to some embodiments of the invention, Q is a substituted or unsubstituted methylene group.

According to some embodiments of the invention, Q is dimethylmethylene (—C(CH$_3$)$_2$—).

According to some embodiments of the invention, J, M and Q are each absent.

According to some embodiments of the invention, K is —C(=O)—C(CH$_3$)$_2$—.

According to some embodiments of the invention, at least one of W$_1$ and W$_2$ is alkyl, alkenyl, alkynyl or acyl, being from 10 to 30 carbon atoms in length.

According to some embodiments of the invention, the lipid moiety comprises at least one fatty acid moiety selected from the group consisting of lauroyl, myristoyl, palmitoyl, stearoyl, palmitoleoyl, oleoyl, and linoleoyl.

According to some embodiments of the invention, a molar ratio of the bilayer-forming lipid and the polymeric compound in a lipid bilayer described herein is in a range of from 5:1 to 5,000:1.

According to some embodiments of the invention, a liposome described herein further comprises at least one functional moiety or agent, bound to a surface of the liposome and/or within a lipid bilayer and/or core of the liposome.

According to some embodiments of the invention, the functional moiety or agent is a therapeutically active agent or moiety thereof, a labeling moiety or agent and/or a targeting moiety or agent.

According to some embodiments of the invention, a carrier as described herein comprises an aqueous liquid.

According to some embodiments of the invention, a lubricant composition as described herein further comprises a water-soluble polymer.

According to some embodiments of the invention, a lubricant composition according to any of the respective embodiments described herein is for lubricating a physiological surface, wherein the carrier is a physiologically acceptable carrier.

According to some embodiments of the invention, a method according to any of the respective embodiments described herein comprises contacting a surface with a composition comprising the liposomes and a carrier.

According to some embodiments of the invention, a method according to any of the respective embodiments described herein further comprises contacting a surface with a water-soluble polymer.

According to some embodiments of the invention, a surface as described herein is a hydrogel surface.

According to some embodiments of the invention, a surface as described herein is a contact lens surface.

According to some embodiments of the invention, a surface as described herein is a physiological surface, and a carrier described herein is a physiologically acceptable carrier.

According to some embodiments of the invention, the surface is an articular surface of a synovial joint.

According to some embodiments of the invention, a liposome, method, medicament and/or composition according to any of the respective embodiments described herein is for use in the treatment of a synovial joint disorder associated with an increased friction coefficient of an articular surface in the synovial joint.

According to some embodiments of the invention, the synovial joint disorder is selected from the group consisting of arthritis, traumatic joint injury, locked joint, and joint injury associated with surgery.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
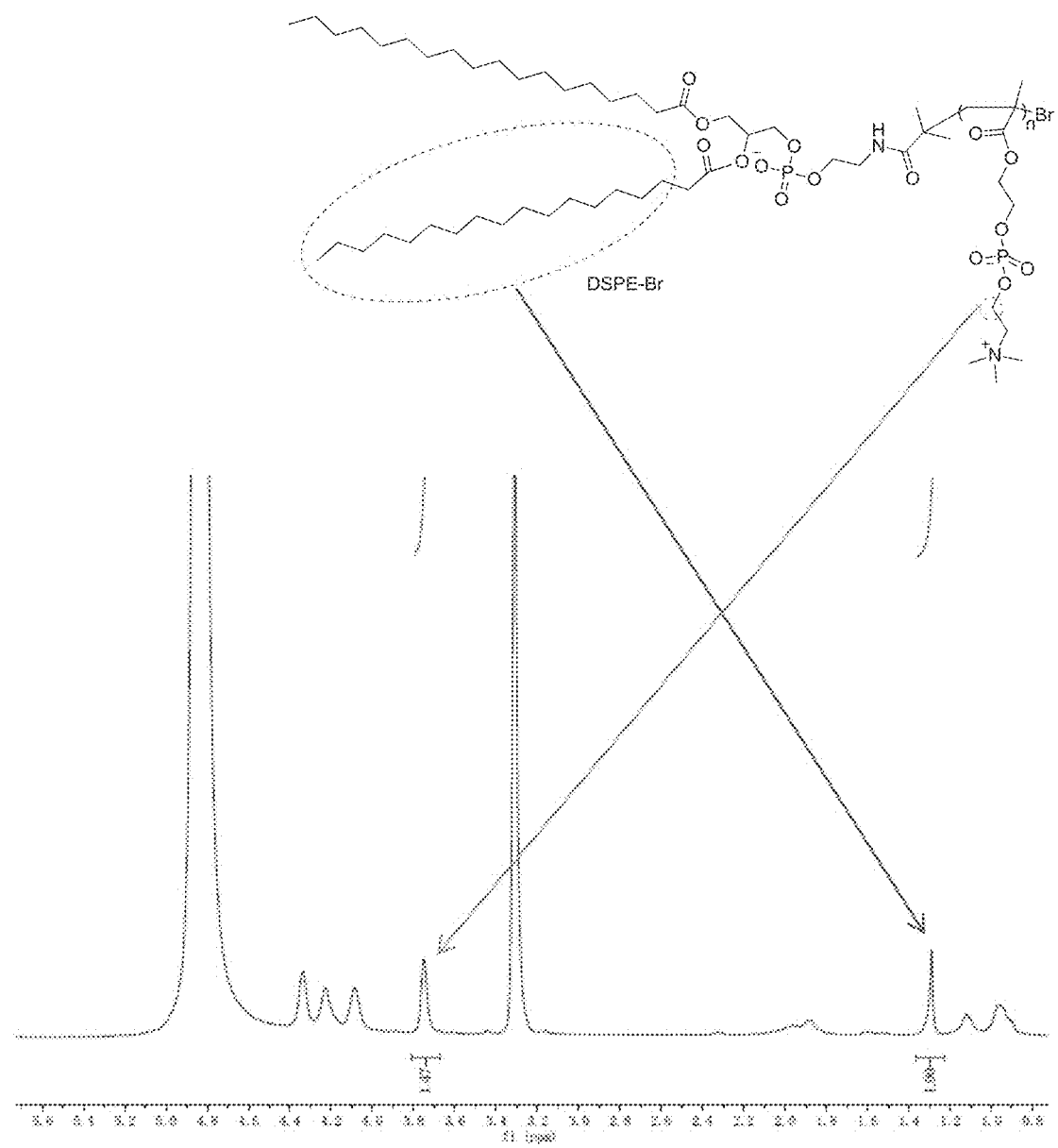
Figure 2:
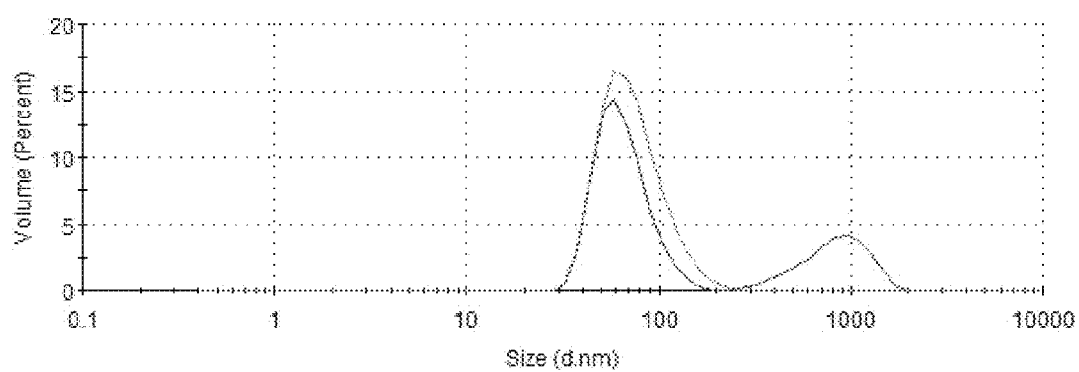
Figure 3:
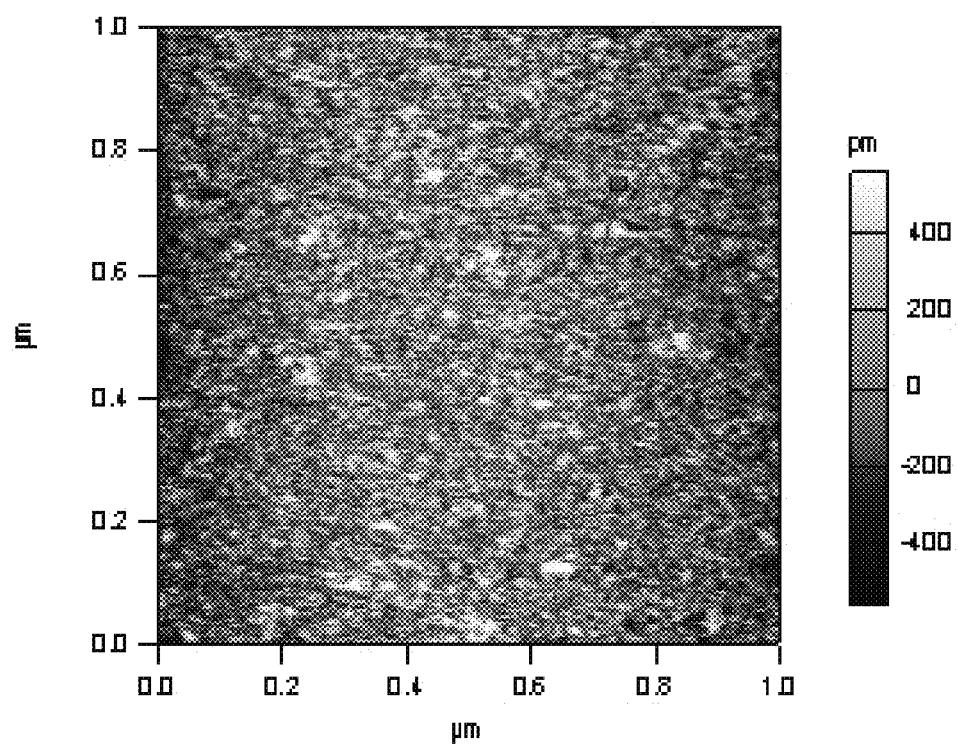
Figure 4:
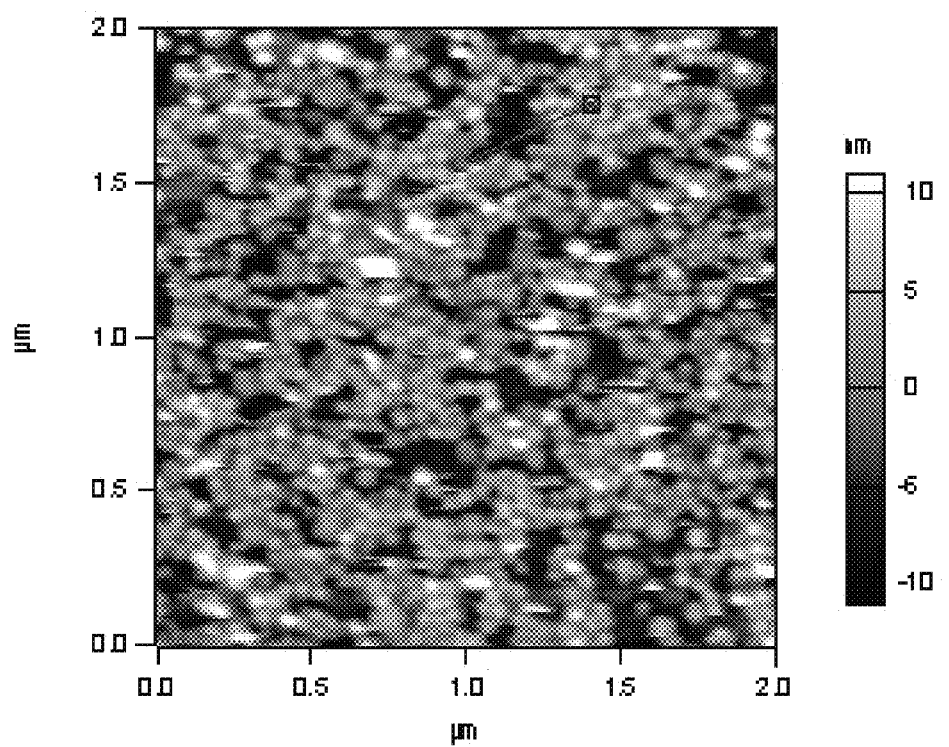
Figure 5A:
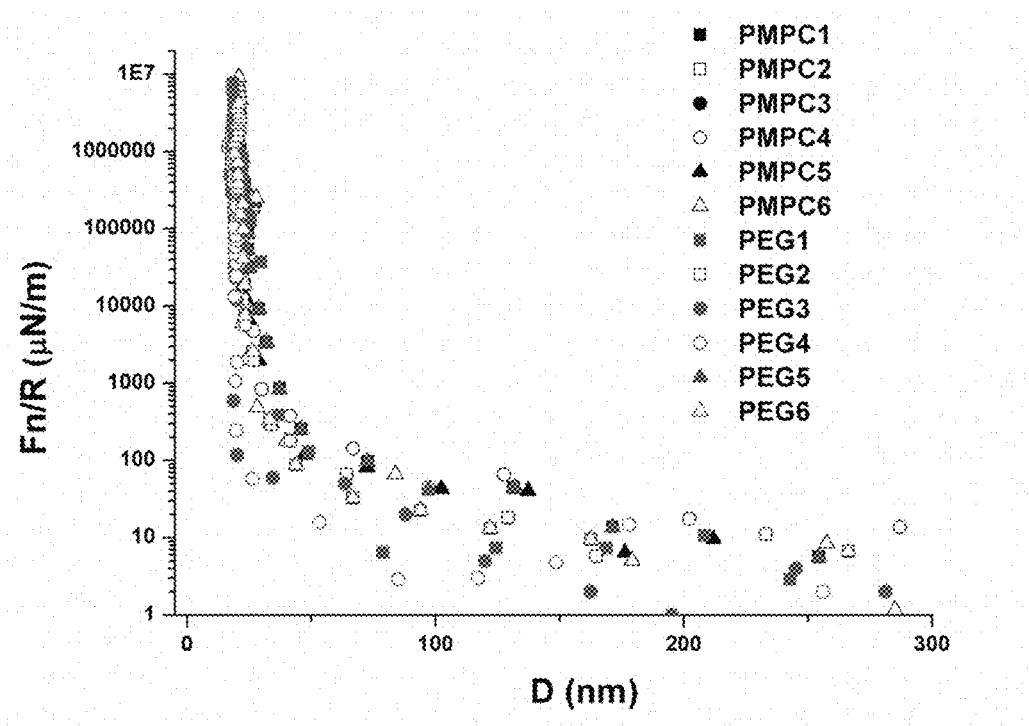
Figure 5B:
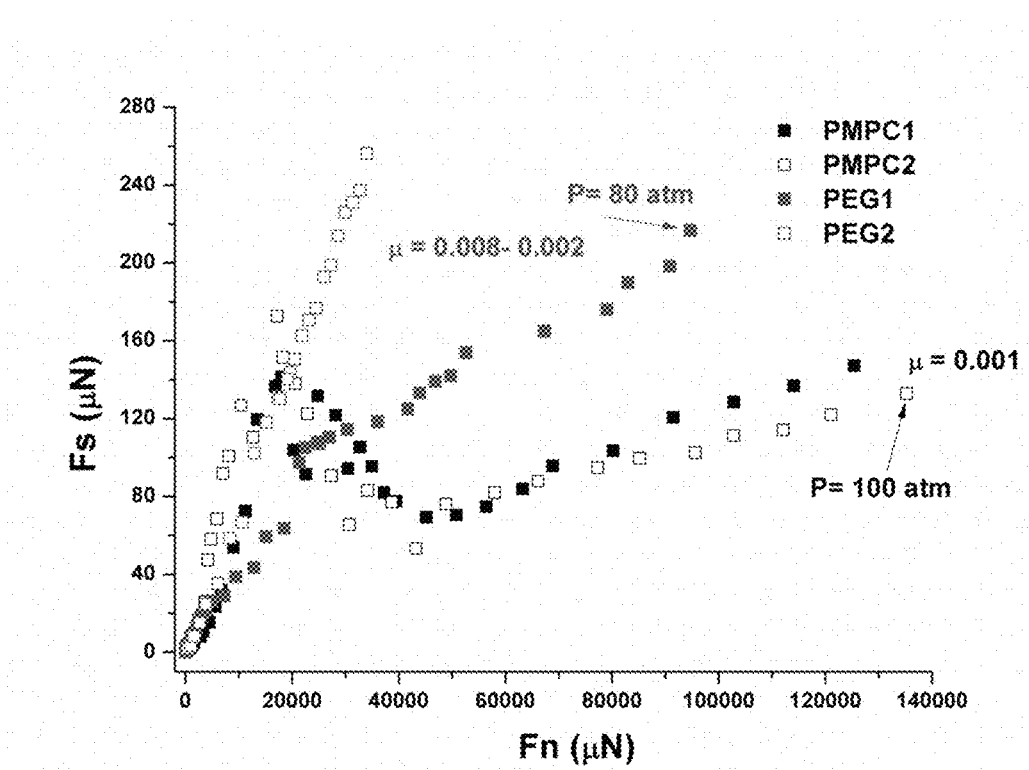
Figure 6A:
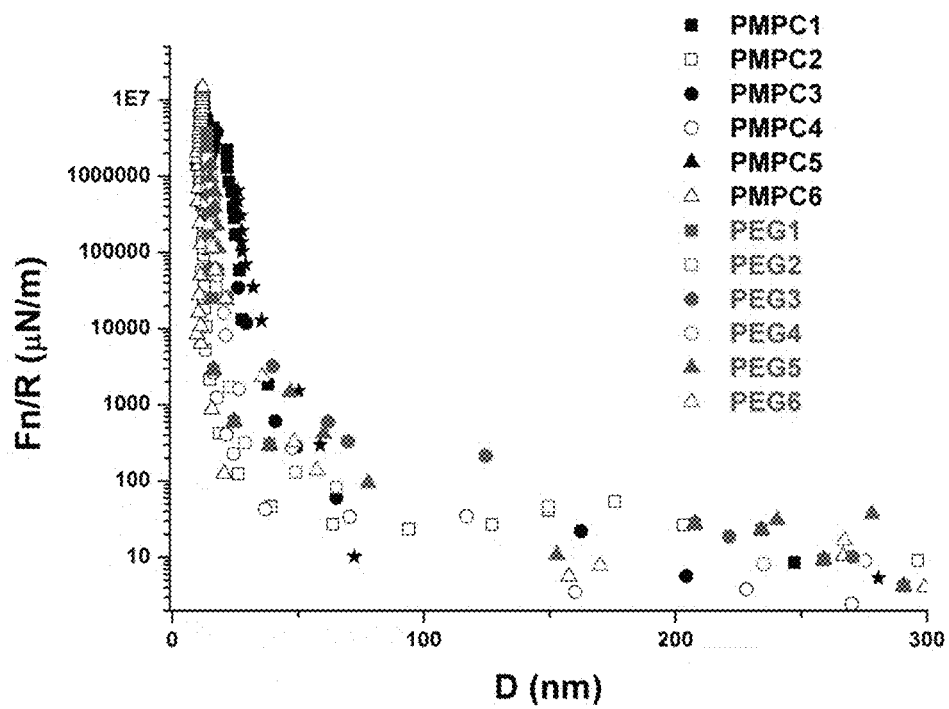
Figure 6B:
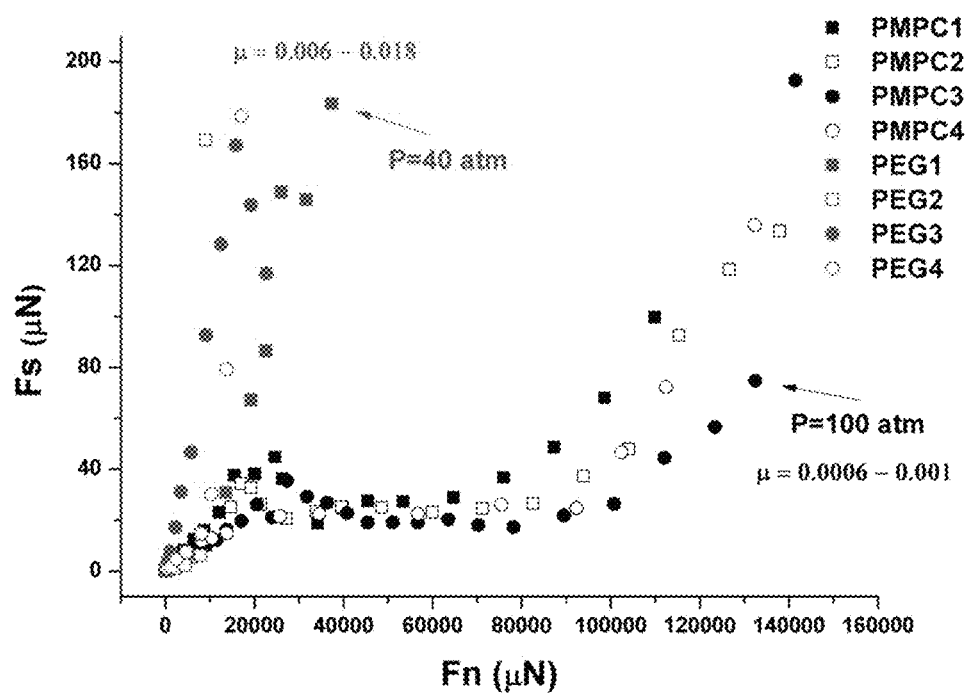
Figure 7:
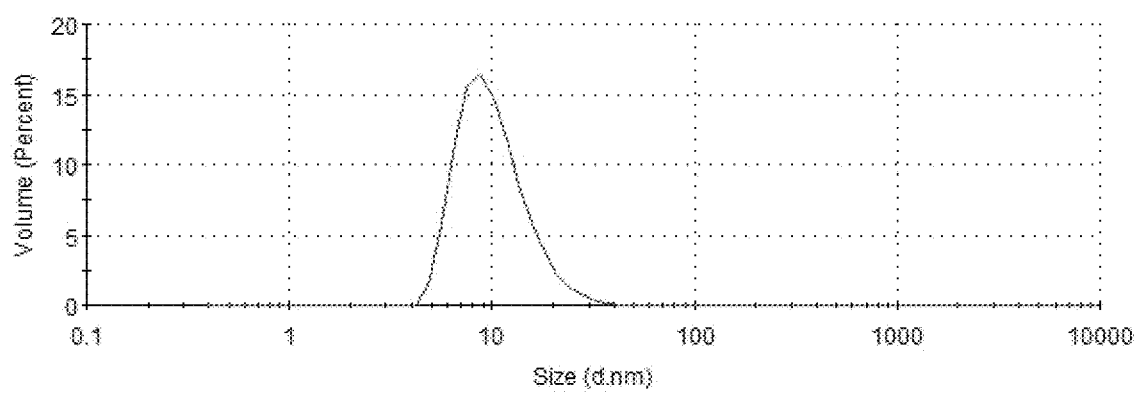
Figure 8A:
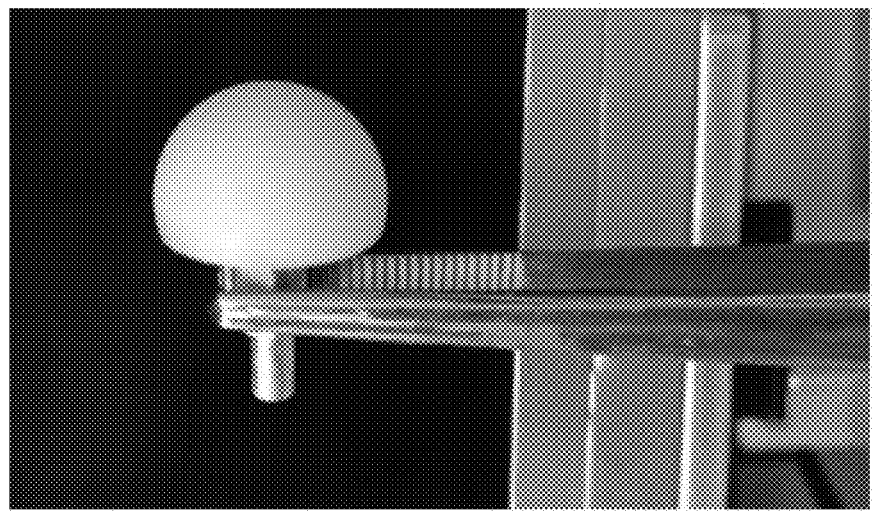
Figure 8B:
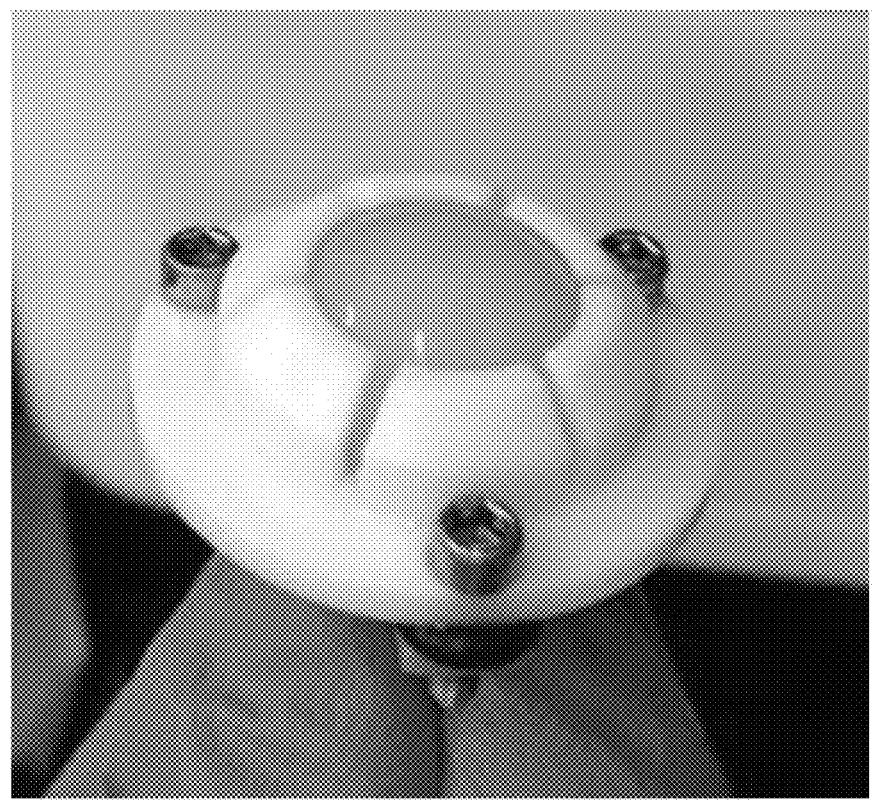
Figure 9:
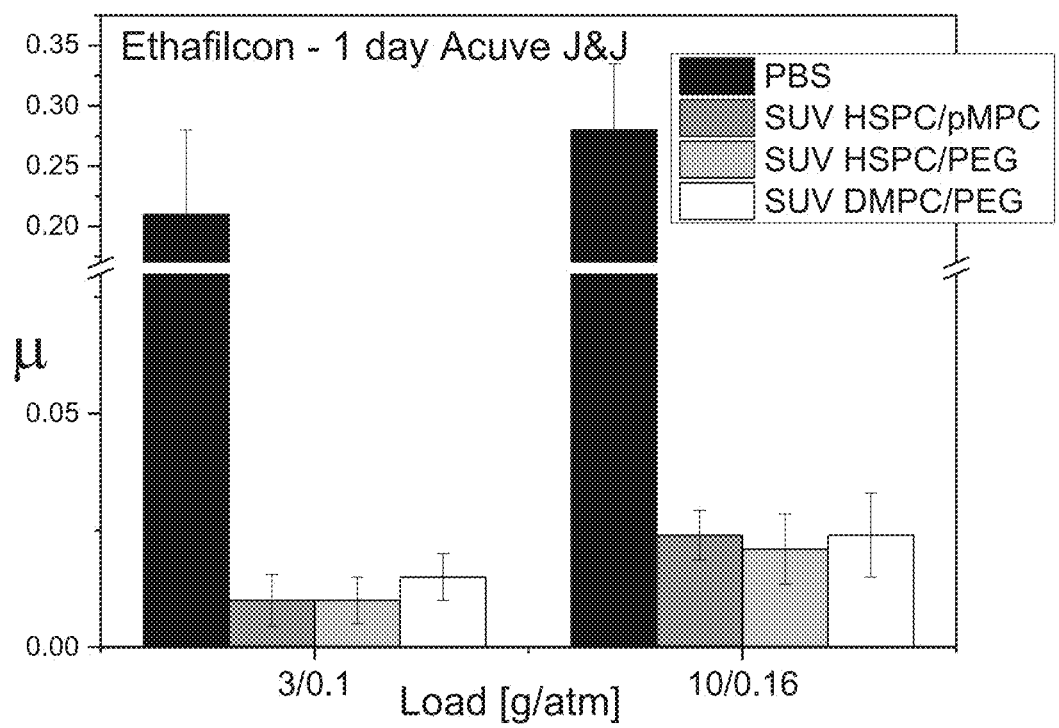
Figure 10:
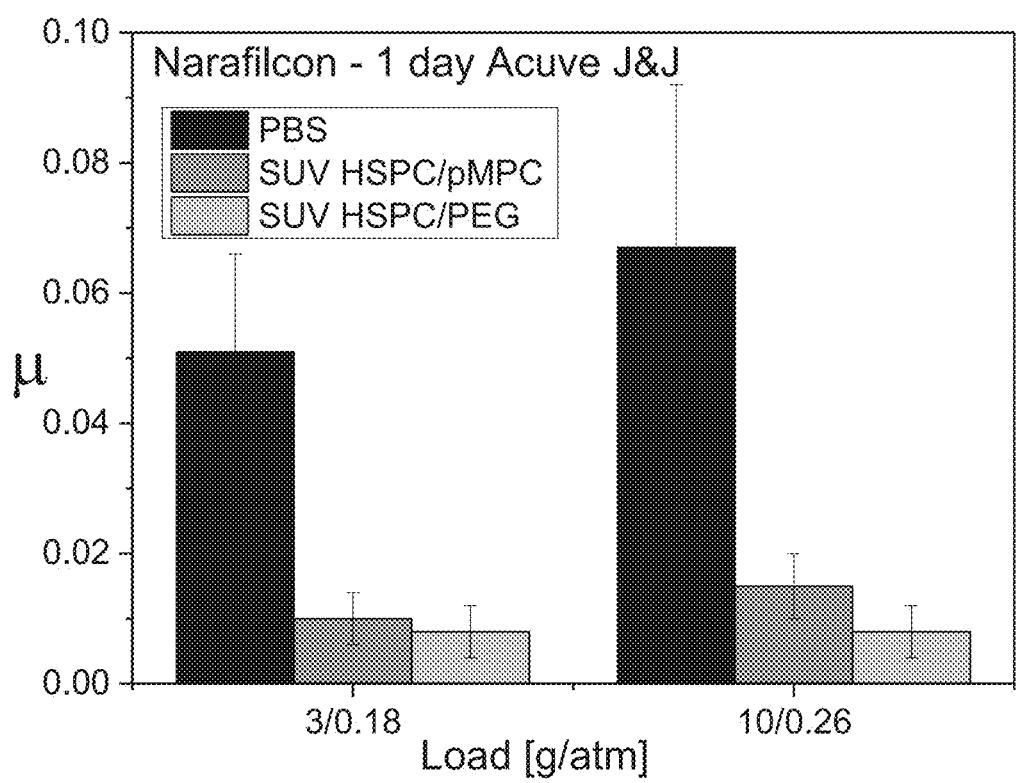
Figure 11:
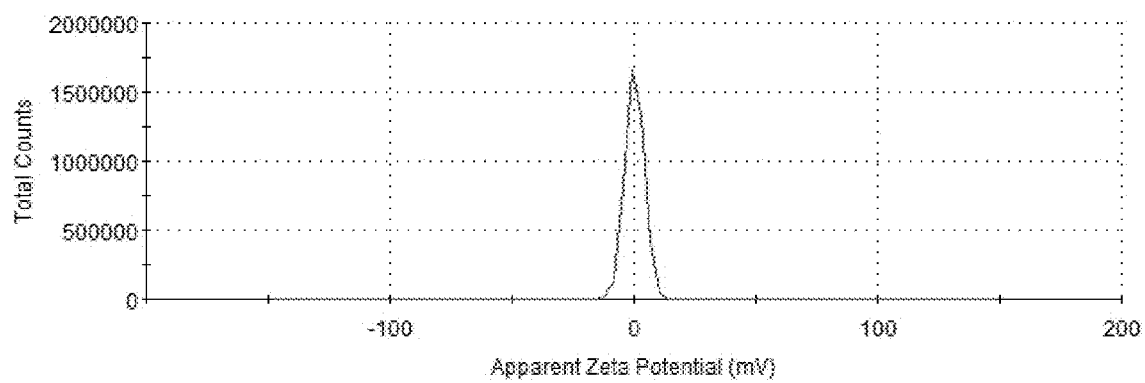
Figure 12:
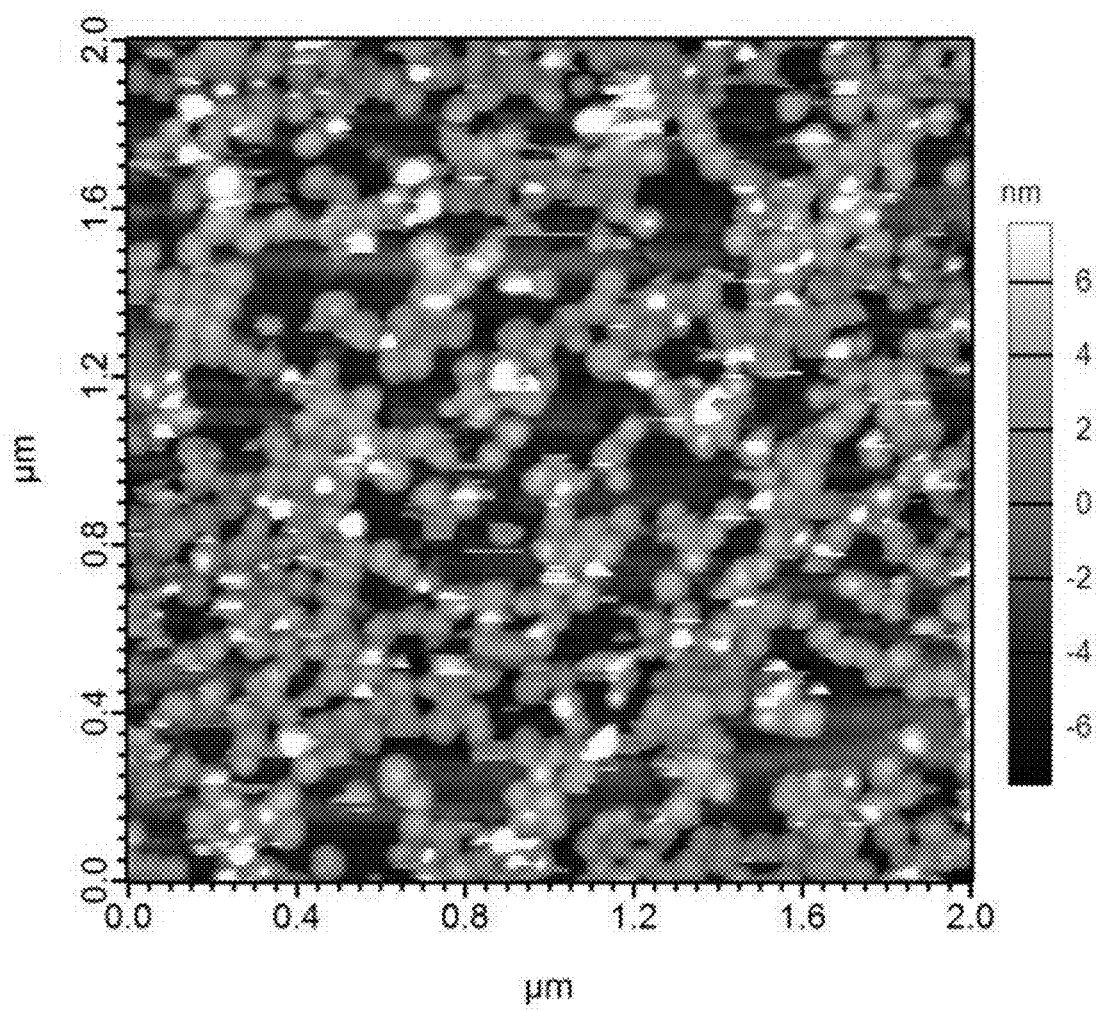
Figure 13:
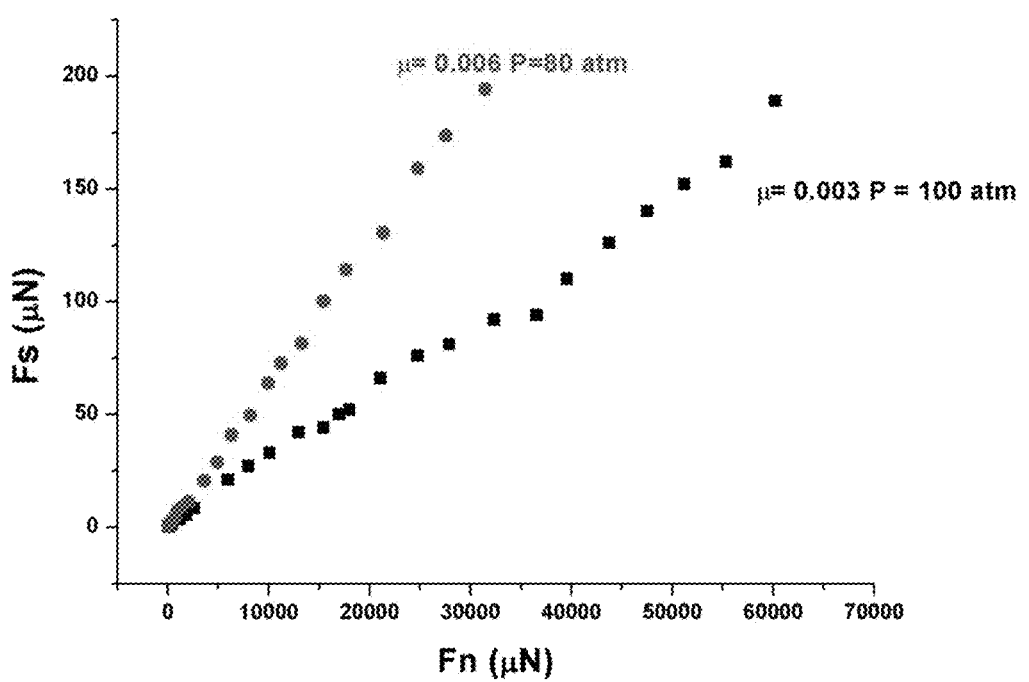

FIG. 1 presents a $^1$H-NMR spectrum and corresponding structure of DSPE-PMPC (distearoylphosphatidylethanolamine-poly((O-(2-methacryloyloxyethyl) phosphorylcholine)) prepared according to exemplary embodiments of the invention;

FIG. 2 is a graph showing distribution of liposome particle size by volume following storage of HSPC (hydrogenated soy phosphatidylcholine) liposomes (red/dark line) and HSPC liposomes with DSPE-PMPC (green/light line) for one month, as determined by dynamic light scattering measurements;

FIG. 3 is an atomic force microscopy (AFM) image of a mica surface after exposure to DSPE-PMPC-stabilized HSPC liposomes in water;

FIG. 4 is an AFM image of a mica surface after exposure to DSPE-PMPC-stabilized HSPC liposomes in water at pH 5 (after which the pH 5 water was replaced by conductivity water (pH 5.8));

FIG. 5A is a graph showing the normal force (normalized as Fn/R in the Derjaguin approximation) as a function of distance (D) between two mica surfaces coated with DSPE-PMPC-stabilized HSPC (PMPC) or DSPE-PEG-stabilized HSPC (PEG) liposomes in conductivity water (filled symbols indicate first approach at a given contact point, corresponding symbols indicate second approach at the same contact point);

FIG. 5B is a graph showing the friction force (Fs) between two mica surfaces coated with DSPE-PMPC-stabilized HSPC liposomes (PMPC) or DSPE-PEG-stabilized HSPC liposomes (PEG) in conductivity water as a function of applied loads (normal force Fn) (filled symbols indicate first approach at a given contact point, corresponding symbols indicate second approach at the same contact point; friction coefficients μ (defined as Fs/Fn) and pressures (P) corresponding to the highest loads attained in a data set are indicated at the end points of the data sets);

FIG. 6A is a graph showing the normal force (normalized as Fn/R in the Derjaguin approximation) as a function of distance (D) between two mica surfaces coated with DSPE-PMPC-stabilized HSPC (PMPC) or DSPE-PEG-stabilized HSPC (PEG) liposomes in aqueous 0.15 M NaNO$_3$ (filled symbols indicate first approach at a given contact point, corresponding symbols indicate second approach at the same contact point);

FIG. 6B is a graph showing the friction force (Fs) between two mica surfaces coated with DSPE-PMPC-stabilized HSPC (PMPC) or DSPE-PEG-stabilized HSPC (PEG) liposomes in aqueous 0.15 M NaNO$_3$ as a function of applied loads (normal force Fn) (filled symbols indicate first approach at a given contact point, corresponding symbols indicate second approach at the same contact point; friction coefficients μ (defined as Fs/Fn) and pressures (P) corresponding to the highest loads attained in a data set are indicated at the end points of the data sets);

FIG. 7 is a is a graph showing distribution of micelle size by volume following incubation of 20 mg/ml DSPE-PMPC in water for one day, as determined by dynamic light scattering measurements;

FIGS. 8A and 8B present photographs of a cornea-mimicking lens holder (FIG. 8A) and the same holder with a soft contact lens mounted in place (FIG. 8B), used in some of the experiments employing a tribometer for measuring friction coefficients of contact lenses described in the Examples section herein;

FIG. 9 is a graph showing the friction coefficient of etafilcon A contact lenses under loads of 3 or 10 grams (corresponding to mean pressures of 0.1 and 0.16 atmospheres, respectively) following incubation for 2 days in PBS with small unilamellar vesicles (SUV) of HSPC and DSPE-PMPC (HSPC/pMPC), HSPC and DSPE-PEG (HSPC/PEG) or DMPC and DPPE-PEG (DMPC/PEG), or in PBS without liposomes (PBS);

FIG. 10 is a graph showing the friction coefficient of narafilcon A contact lenses under loads of 3 or 10 grams (corresponding to mean pressures of 0.18 and 0.26 atmospheres, respectively) following incubation for 2 days in PBS with small unilamellar vesicles (SUV) of HSPC and DSPE-PMPC (HSPC/pMPC) or HSPC and DSPE-PEG (HSPC/PEG), or in PBS without liposomes (PBS);

FIG. 11 is a histogram showing the distribution of apparent zeta potential of small unilamellar vesicles (SUV) of HSPC and DSG-PMPC (1,2-distearoyl-sn-glycerol-poly((O-(2-methacryloyloxyethyl) phosphorylcholine)) prepared according to exemplary embodiments of the invention;

FIG. 12 is an AFM image of a mica surface after exposure to DSG-PMPC-stabilized HSPC liposomes in water (pH 5.8); and FIG. 13 is a graph showing the friction force (Fs) between two mica surfaces coated with DSG-PMPC-stabilized HSPC liposomes in water as a function of applied loads (normal force Fn) (friction coefficients μ (defined as Fs/Fn) and pressures (P) corresponding to the highest loads attained in a data set are indicated at the end points of the data sets).

DESCRIPTION OF SPECIFIC EMBODIMENTS OF THE INVENTION

The present invention, in some embodiments thereof, relates to material science and, more particularly, but not exclusively, to novel polymeric compounds usable, inter alia, for forming liposomes.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In a search for polymeric compounds capable of stabilizing lipid layers such as those of liposomes, the present inventors have designed compounds comprising a lipid moiety and a polymeric moiety in which monomers include both phosphate and ammonium ionic groups, which are similar to phosphocholine and related head groups of liposome-forming phospholipids such as phosphatidylcholines.

While reducing the present invention to practice, the inventors have uncovered that liposomes containing even small amounts of such a lipid-containing polymeric compound exhibit considerably enhanced stability and are highly effective lubricants between sliding surfaces, being more effective lubricants than liposomes conjugated to PEG, particularly in a saline environment (e.g., a physiological environment) and/or at high pressures.

The inventors have further uncovered that such lipid-containing polymeric compounds per se form stable micelles in an aqueous environment.

Embodiments of the present invention therefore relate to polymeric compounds which bear phosphocholine analogs as pendant groups and are conjugated to a lipid (e.g., phospholipid) moiety. Exemplary such polymeric compounds are represented by formula I. These polymeric compounds are also referred to herein as "lipid-containing polymeric compounds" or simply as "polymeric compounds".

The lipid-containing polymeric compounds disclosed herein are capable of stabilizing liposomes used for various applications (including in vivo applications) against aggregation and fusion, thereby increasing shelf life, while retaining and even enhancing properties associated with the surfaces of liposomes and other phospholipid layers, such as biocompatibility, a high degree of hydration, and lubricant activity (e.g., by hydration lubrication). The disclosed polymeric compounds per se are also capable of forming stable micelles in an aqueous environment which can be used as stable replacement for liposomes in various applications (including in vivo applications), such as lubrication, including lubrication of interfaces with physiological surfaces.

According to an aspect of some embodiments of the invention, there is provided a polymeric compound having the general formula I:

Formula I wherein:
m is zero or a positive integer;
n is an integer which is at least 1;
X is a lipid moiety, wherein when X does not comprise a phosphate group, n is at least 2;
Y is a backbone unit which forms a polymeric backbone;
L is absent or is a linking moiety; and
Z has the general formula II:

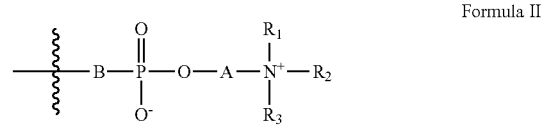

Formula II wherein:

A is a substituted or unsubstituted hydrocarbon;

B is an oxygen atom or is absent; and $R_1$-$R_3$ are each independently hydrogen, alkyl, cycloalkyl, heteroalicyclic, aryl or heteroaryl, as described in more detail herein below.

Formula I may also be described herein simply as:

X—[Y(-L-Z)]n[Y]m which is to be regarded as interchangeable with the schematic depiction hereinabove.

Polymeric Moiety:

Herein, the term "polymeric" refers a compound having at least 2 repeating units (and more preferably at least 3 repeating units), the repeating units being identical or similar. It is to be appreciated that the compound of general formula I is by definition polymeric when n is at least 2, as it comprises at least 2 of the backbone units represented by Y.

Herein, the phrase "polymeric moiety" refers to the portion of the polymeric compound (according to any of the embodiments described herein relating to general formula I) which has the general formula Ia:

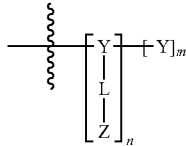

Formula Ia wherein m, n, Y, L and Z are as defined herein for general formula I.

Formula Ia may also be described herein simply as:

[Y(-L-Z)]n[Y]m which is to be regarded as interchangeable with the schematic depiction hereinabove.

Herein, the phrase "polymeric compound" further encompasses compounds having a "polymeric moiety" as described herein having one unit (e.g., according to formula Ia wherein n is 1), provided that the lipid moiety described herein (e.g., the lipid moiety represented by X) has a similar unit. For example, when the lipid moiety comprises a phosphate group (e.g., the lipid moiety is a glycerophospholipid moiety), such that the lipid moiety has a phosphate group and a single unit of the polymeric moiety has a phosphate group, the two phosphate groups may be regarded as repeating units.

In preferred embodiments however, n is at least 2, such that the polymeric moiety per se has at least two units. In some embodiments, n is at least 3.

As used herein, the term "backbone unit" refers to a repeating unit, wherein linkage of a plurality of the repeating unit (e.g., sequential linkage) forms a polymeric backbone. A plurality of linked repeating units per se is also referred to herein as a "polymeric backbone".

As shown in formulas I and Ia, L and Z together form a pendant group of at least a portion of the backbone units, which group is referred to herein for brevity simply as the "pendant group".

Each backbone unit Y with pendant group (i.e., a unit represented by Y(-L-Z), the number of which is represented by the variable n) and each backbone unit Y without a pendant group (the number of which is represented by the variable m) is also referred to herein as a "monomeric unit".

A backbone unit may optionally be a residue of a polymerizable monomer or polymerizable moiety of a monomer. A wide variety of polymerizable monomers and moieties will be known to the skilled person, and the structure of the residues of such monomers which result upon polymerization (e.g., monomeric units) will also be known to the skilled person.

A "residue of a polymerizable monomer" refers to a modified form of a polymerizable monomer and/or a portion of a polymerizable monomer that remains after polymerization.

A portion of a polymerizable monomer may be formed, for example, by a condensation reaction, e.g., wherein at least one atom or group (e.g., a hydrogen atom or hydroxyl group) in the monomer, and optionally at least two atoms or groups (e.g., a hydrogen atom and a hydroxyl group) in the monomer, is replaced with a covalent bond with another polymerizable monomer.

A modified form of a polymerizable monomer may be formed, for example, by ring-opening (wherein a covalent bond between two atoms in a ring is broken, and the two atoms optionally each become linked to another polymerizable monomer); and/or by adding to an unsaturated bond, wherein an unsaturated bond between two adjacent atoms is broken (e.g., conversion of an unsaturated double bond to a saturated bond, or conversion of an unsaturated triple bond to an unsaturated double bond) and the two atoms optionally each become linked to another polymerizable monomer.

A modified form of a polymerizable monomer may consist essentially of the same atoms as the original monomer, for example, different merely in the rearrangement of covalent bonds, or alternatively, may have a different atomic composition, for example, wherein polymerization includes a condensation reaction (e.g., as described herein).

Examples of backbone units include, without limitation, substituted or unsubstituted hydrocarbons (which may form a substituted or unsubstituted hydrocarbon backbone), such as alkylene units; hydroxycarboxylic acid units (which may form a polyester backbone), e.g., glycolate, lactate, hydroxybutyrate, hydroxyvalerate, hydroxycaproate and hydroxybenzoate units; dicarboxylic acid units (which may form a polyester backbone in combination with a diol and/or a polyamide in combination with a diamine), e.g., adipate, succinate, terephthalate and naphthalene dicarboxylic acid units; diol units (which may form a polyether backbone, or form a polyester backbone in combination with a dicarboxylic acid), e.g., ethylene glycol, 1,2-propanediol, 1,3-propanediol, 1,4-butanediol, and bisphenol A units; diamine units (which may form a polyamide backbone in combination with a dicarboxylic acid), e.g., para-phenylene diamine and alkylene diamines such hexylene diamine; carbamate units (which may form a polyurethane backbone); amino acid residues (which may form a polypeptide backbone); and saccharide residues (which may form a polysaccharide backbone).

In some embodiments of any of the embodiments described herein, Y is a substituted or unsubstituted alkylene unit.

In some embodiments, Y is a substituted or unsubstituted ethylene unit, that is, an alkylene unit 2 atoms in length.

Polymeric backbones wherein Y is a substituted or unsubstituted ethylene unit may optionally be a polymeric backbone such as formed by polymerizing ethylene ($CH_2$=$CH_2$) and/or substituted derivatives thereof (also referred to herein as "vinyl monomers"). Such polymerization is a very wellstudied procedure, and one of ordinary skill in the art will be aware of numerous techniques for effecting such polymerization.

It is to be understood that any embodiments described herein relating to a polymeric backbone formed by a polymerization encompass any polymeric backbone having a structure which can be formed by such polymerization, regardless of whether the polymeric backbone was formed in practice by such polymerization (or any other type of polymerization).

As is well known in the art, the unsaturated bond of ethylene and substituted ethylene derivatives becomes saturated upon polymerization, such that the backbone units in a polymeric backbone are saturated, although they may be referred to as units of an unsaturated compound (e.g., a "vinyl monomer" or "olefin monomer") to which they are analogous.

Polymers which can be formed from unsaturated monomers such as vinyl monomers and olefin monomers are also referred to by the terms "polyvinyl" and "polyolefin".

Herein, an "unsubstituted" alkylene unit (e.g., ethylene unit) refers to an alkylene unit which does not have any substituent other than the pendant group discussed herein (represented as (-L-Z)). That is, an alkylene unit attached to the aforementioned pendant group is considered unsubstituted if there are no substituents at any other positions on the alkylene unit.

In some embodiments of any of the embodiments described herein, Y has the formula —$CR_4R_5$—$CR_6D$-.

When Y is a backbone unit which is not attached to L or Z (i.e., to a pendant group described herein), D is $R_7$ (an end group, as defined herein); and when Y is a backbone unit which is attached to L or Z, D is a covalent bond or a linking group attaching Y to L or Z. The linking group may optionally be —O—, —S—, arylene, sulfinyl, sulfonyl, phosphate, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, or amino.

$R_4$-$R_7$ are each independently hydrogen, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, azo, phosphate phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, or amino.

Herein, the phrase "linking group" describes a group (e.g., a substituent) that is attached to two or more moieties in the compound.

Herein, the phrase "end group" describes a group (e.g., a substituent) that is attached to a single moiety in the compound via one atom thereof.

When each of $R_4$-$R_6$ is hydrogen, and D is a covalent bond or linking group, Y is an unsubstituted ethylene group attached (via D) to a pendant group described herein.

When each of $R_4$-$R_7$ is hydrogen (and D is $R_7$), Y is an unsubstituted ethylene group which is not attached to a pendant group described herein.

In some embodiments of any of the embodiments described herein, $R_4$ and $R_5$ are each hydrogen. Such embodiments include polymeric backbones formed from many widely used vinyl monomers (including ethylene), including, for example, olefins (e.g., ethylene, propylene, 1-butylene, isobutylene, 4-methyl-1-pentene), vinyl chloride, styrene, vinyl acetate, acrylonitrile, acrylate and derivatives thereof (e.g., acrylate esters, acrylamides), and methacrylate and derivatives thereof (e.g., methacrylate esters, methacrylamides).

In some embodiments of any of the embodiments described herein, $R_6$ is hydrogen. In some such embodiments, $R_4$ and $R_5$ are each hydrogen.

In some embodiments of any of the embodiments described herein, $R_6$ is methyl. In some such embodiments, $R_4$ and $R_5$ are each hydrogen. In some such embodiments, the backbone unit is a unit of methacrylate or a derivative thereof (e.g., methacrylate ester, methacrylamide).

In some embodiments of any of the embodiments described herein, the linking group represented by the variable D is —O—, —C(=O)O—, —C(=O)NH— or phenylene. In exemplary embodiments, D is —C(=O)O—.

For example, the backbone unit may optionally be a vinyl alcohol derivative (e.g., an ester or ether of a vinyl alcohol unit) when D is —O—; an acrylate or methacrylate derivative (e.g., an ester of an acrylate or methacrylate unit) when D is —C(=O)O—; an acrylamide or methacrylamide unit when D is —C(=O)NH—; and/or a styrene derivative (e.g., a substituted styrene unit) when D is phenylene.

In some embodiments of any of the embodiments described herein, L is a substituted or unsubstituted hydrocarbon from 1 to 10 carbon atoms in length. In some embodiments, the hydrocarbon is unsubstituted. In some embodiments, the hydrocarbon is a linear, unsubstituted hydrocarbon, that is, —$(CH_2)_i$— wherein i is an integer from 1 to 10.

In some embodiments of any of the embodiments described herein, L is a substituted or unsubstituted ethylene group. In some embodiments, L is an unsubstituted ethylene group (—$CH_2CH_2$—).

In some embodiments of any of the embodiments described herein, B is an oxygen atom. In some such embodiments, L is a hydrocarbon according to any of the respective embodiments described herein (i.e., L is not absent), and Z is a phosphate group attached to L.

In some embodiments of any of the embodiments described herein, B is absent. In some such embodiments, L is a hydrocarbon according to any of the respective embodiments described herein (i.e., L is not absent), and Z is a phosphonate group attached to L. In some embodiments, L is also absent, such that the phosphorus atom of formula II is attached directly to Y.

In some embodiments of any of the embodiments described herein, A is a substituted or unsubstituted hydrocarbon from 1 to 4 carbon atoms in length.

In some embodiments of any of the embodiments described herein, A is an unsubstituted hydrocarbon. In some such embodiments, the unsubstituted hydrocarbon is from 1 to 4 carbon atoms in length. In some embodiments, the hydrocarbon is a linear, unsubstituted hydrocarbon, that is, —$(CH_2)_j$— wherein j is an integer from 1 to 4.

In some embodiments of any of the embodiments described herein, A is a substituted or unsubstituted ethylene group.

In some embodiments of any of the embodiments described herein, A is an unsubstituted ethylene group (—$CH_2CH_2$—). In such embodiments, the moiety having general formula II (represented by the variable Z) is similar or identical to a phosphoethanolamine or phosphocholine moiety. Phosphoethanolamine and phosphocholine moieties are present in many naturally occurring compounds (e.g., phosphatidylcholines, phosphatidylethanolamines).

In some embodiments of any of the embodiments described herein, A is an ethylene group substituted by a C-carboxy group. In some embodiments, the C-carboxy is attached to the carbon atom adjacent to the nitrogen atom depicted in formula II (rather than the carbon atom attached to the depicted oxygen atom). In such embodiments, the moiety having general formula II (represented by the variable Z) is similar or identical to a phosphoserine moiety. Phosphoserine is present in many naturally occurring compounds (e.g., phosphatidylserines).

Without being bound by any particular theory, it is believed that moieties similar or identical to naturally occurring moieties such as phosphocholine, phosphoethanolamine and/or phosphoserine may be particularly biocompatible.

In some embodiments of any of the embodiments described herein, $R_1$-$R_3$ (the substituents of the nitrogen atom depicted in general formula II) are each independently hydrogen or $C_{1-4}$-alkyl. In some embodiments, $R_1$-$R_3$ are each independently hydrogen or methyl. In some embodiments, $R_1$-$R_3$ are each methyl. In some such embodiments, $R_1$-$R_3$ are each hydrogen.

The variable n may be regarded as representing a number of backbone units (represented by the variable Y) which are substituted by the pendant group represented by (-L-Z), and the variable m may be regarded as representing a number of backbone units which are not substituted by such a pendant group. The sum n+m may be regarded as representing the total number of backbone units in the polymeric backbone. The ratio n/(n+m) may be regarded as representing the fraction of backbone units which are substituted by the pendant group represented by (-L-Z).

The backbone unit Y substituted by the pendant group may be the same as or different than the backbone unit Y which is not substituted by the pendant group (e.g., when m is at least 1).

The plurality (indicated by the variable n) of backbone units Y substituted by the pendant group may be the same as each other or different from each other.

In addition, the plurality (indicated by the variable n) of pendant groups (-L-Z) attached to a plurality of backbone units Y may be the same as each other or different from each other (e.g., may differ in the identity of any one or more of A, B, $R_1$, $R_2$, $R_3$ and L).

In any of the embodiments described herein wherein more than one backbone unit Y is not substituted by the pendant group described herein (i.e., when m is more than 1), the plurality (indicated by the variable m) of backbone units Y which are substituted by the pendant group may be the same as each other or different from each other.

The number of types of backbone units substituted by the pendant group, the number of types of backbone units not substituted by the pendant group (if any such units are present), and/or the number of types of pendant group in the polymeric moiety may each independently be any number (e.g., 1, 2, 3, 4, 5, 6, 7, 8, 9, 10 or more).

In some embodiments of any of the embodiments described herein, the polymeric moiety is a copolymer moiety, that is, the polymeric moiety comprises at least two different types of monomeric unit. The different types of monomeric unit may differ in whether they comprise the pendant group (-L-Z) according to any of the respective embodiments described herein (e.g., when m is at least 1), differ in the type of backbone unit Y, and/or differ in the type of pendant group (-L-Z).

For example, in some embodiments of any of the embodiments described herein the backbone unit Y in each of the Y(-L-Z) units may optionally be the same or different, while the L and Z moieties are the same among the Y(-L-Z) units. In some such embodiments, backbone units not substituted by the pendant group (if any such units are present) may optionally be the same as backbone unit Y in each of the Y(-L-Z) units. Alternatively, backbone units not substituted by the pendant group (if any such units are present) may optionally be different than backbone unit Y in each of the Y(-L-Z) units (while optionally being the same among all backbone units not substituted by the pendant group).

In some embodiments of any of the embodiments described herein the L moiety in each of the Y(-L-Z) units may optionally be the same or different, while the backbone units Y and the Z moieties are the same among the Y(-L-Z) units. In some such embodiments, backbone units not substituted by the pendant group (if any such units are present) may optionally be the same as backbone unit Y in each of the Y(-L-Z) units. Alternatively, backbone units not substituted by the pendant group (if any such units are present) may optionally be different than backbone unit Y in each of the Y(-L-Z) units (while optionally being the same among all backbone units not substituted by the pendant group).

In some embodiments of any of the embodiments described herein the Z moiety in each of the Y(-L-Z) units may optionally be the same or different, while the backbone units Y and the Z moieties are the same among the Y(-L-Z) units. In some such embodiments, backbone units not substituted by the pendant group (if any such units are present) may optionally be the same as backbone unit Y in each of the Y(-L-Z) units. Alternatively, backbone units not substituted by the pendant group (if any such units are present) may optionally be different than backbone unit Y in each of the Y(-L-Z) units (while optionally being the same among all backbone units not substituted by the pendant group).

In any of the embodiments described herein wherein the polymeric moiety is a copolymer moiety, any two or more different types of monomeric unit may be distributed randomly or non-randomly throughout the polymeric moiety. When different types of monomeric unit are distributed non-randomly, the copolymer may be one characterized by any non-random distribution, for example, an alternating copolymer, a periodic copolymer, and/or a block copolymer.

In some embodiments of any of the embodiments described herein, at least a portion of the monomeric units of the polymeric moiety comprise a targeting moiety (according to any of the embodiments described herein relating to a targeting moiety).

A targeting moiety may optionally be comprised by a backbone unit Y according to any of the respective embodiments described herein, linking moiety L according to any of the respective embodiments described herein, and/or moiety Z according to any of the respective embodiments described herein, for example, wherein a substituent according to any of the respective embodiments described herein comprises (and optionally consists of) the targeting moiety. For example, in some embodiments wherein at least a portion of backbone units Y have the formula —$CR_4R_5$—$CR_6D$- (as described herein in any of the respective embodiments), any one or more of $R_4$-$R_6$ and D (optionally wherein D is $R_7$ as described herein) comprises a targeting moiety according to any of the respective embodiments described herein (e.g., wherein any one or more of $R_4$-$R_6$ and D is a substituted group, comprising a substituent which is a targeting moiety), and optionally any one or more $R_4$-$R_6$ and D is a targeting moiety. However, many other structures of monomeric units comprising a substituent which comprises (and optionally consist of) a targeting moiety are also encompassed by embodiments of the invention.

When Y is a backbone unit which is not attached to L or Z (i.e., to a pendant group as described herein), D is $R_7$ (an end group, as defined herein); and when Y is a backbone unit which is attached to L or Z, D is a covalent bond or a linking group attaching Y to L or Z. The linking group may optionally be —O—, —S—, arylene, sulfinyl, sulfonyl, phosphate, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, or amino.

$R_4$-$R_7$ are each independently hydrogen, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, azo, phosphate phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, or amino.

In some embodiments, the polymeric moiety is a copolymer moiety wherein at least one type of monomeric unit comprises a targeting moiety (according to any of the respective embodiments described herein) and at least one type of monomeric unit does not comprise such a targeting moiety. The distribution of a monomeric unit comprising a targeting moiety may be in accordance with any distribution described herein of a monomeric unit in a copolymer moiety (e.g., random, alternating, periodic copolymer, and/or block copolymer).

In some embodiments of any of the embodiments described herein wherein a portion of monomeric units comprise a targeting moiety, the monomeric units comprising a targeting moiety are, on average, closer to a terminus of the polymeric moiety distal to the lipid moiety, e.g., an average distance (as measured in atoms or backbone units along the backbone of the polymeric moiety) of monomeric units comprising a targeting moiety from the lipid moiety is greater than an average distance of the other monomeric units from the lipid moiety.

In some embodiments, at least a portion (and optionally all) of the monomeric units comprising a targeting moiety form a block (of one or more monomeric units) near (and optionally at) a terminus of the polymeric moiety distal to the lipid moiety. In some such embodiments, the copolymer moiety contains a single monomeric unit which comprises a targeting moiety, and said monomeric unit is at a terminus of the polymeric moiety distal to the lipid moiety.

Without being bound by any particular theory, it is assumed that a targeting moiety located distal to the lipid moiety may be more effective as a targeting moiety (e.g., more effective at binding to a target), for example, due to the targeting moiety being less sterically shielded (e.g., by a surface to which the lipid moiety is associated) and therefore more exposed to and thus better able to make contact with targets in an aqueous environment.

In alternative embodiments, the polymeric moiety does not comprise a targeting moiety described herein according to any of the respective embodiments.

In some embodiments of any of the embodiments described herein, the percentage of backbone units (represented by the variable Y) which are substituted by the pendant group represented by (-L-Z) (as represented by the formula $100\%*n/(n+m)$) is at least 20%. In some embodiments, the percentage of backbone units substituted by the aforementioned pendant group is at least 30%. In some embodiments, the percentage of backbone units substituted by the aforementioned pendant group is at least 40%. In some embodiments, the percentage of backbone units substituted by the aforementioned pendant group is at least 50%. In some embodiments, the percentage of backbone units substituted by the aforementioned pendant group is at least 60%. In some embodiments, the percentage of backbone units substituted by the aforementioned pendant group is at least 70%. In some embodiments, the percentage of backbone units substituted by the aforementioned pendant group is at least 80%. In some embodiments, the percentage of backbone units substituted by the aforementioned pendant group is at least 90%. In some embodiments, the percentage of backbone units substituted by the aforementioned pendant group is at least 95%. In some embodiments, the percentage of backbone units substituted by the aforementioned pendant group is at least 98%.

In some embodiments of any of the embodiments described herein, m is 0, such that each of the backbone units (represented by the variable Y) is substituted by the pendant group represented by (-L-Z).

In some embodiments of any of the embodiments described herein, n is at least 5. In some embodiments, n is at least 10. In some embodiments, n is at least 15.

In some embodiments of any of the embodiments described herein, n is in a range of from 2 to 1,000. In some embodiments of any of the embodiments described herein, n is in a range of from 2 to 500. In some embodiments of any of the embodiments described herein, n is in a range of from 2 to 200. In some embodiments of any of the embodiments described herein, n is in a range of from 2 to 100. In some embodiments of any of the embodiments described herein, n is in a range of from 2 to 50. In some such embodiments, m is 0.

In some embodiments of any of the embodiments described herein, n is in a range of from 3 to 1,000. In some embodiments of any of the embodiments described herein, n is in a range of from 3 to 500. In some embodiments of any of the embodiments described herein, n is in a range of from 3 to 200. In some embodiments of any of the embodiments described herein, n is in a range of from 3 to 100. In some embodiments of any of the embodiments described herein, n is in a range of from 3 to 50. In some embodiments of any of the embodiments described herein, n is in a range of from 5 to 50. In some embodiments of any of the embodiments described herein, n is in a range of from 10 to 50. In some embodiments of any of the embodiments described herein, n is in a range of from 10 to 25. In some such embodiments, m is 0.

In some embodiments of any of the embodiments described herein, m is in a range of from 0 to 1,000. In some such embodiments, n is in a range of from 2 to 1,000, such that the total number of backbone units is in a range of from 2 to 2,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

In some embodiments of any of the embodiments described herein, m is in a range of from 0 to 500. In some such embodiments, n is in a range of from 2 to 1,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

In some embodiments of any of the embodiments described herein, m is in a range of from 0 to 200. In some such embodiments, n is in a range of from 2 to 1,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

In some embodiments of any of the embodiments described herein, m is in a range of from 0 to 100. In some such embodiments, n is in a range of from 2 to 1,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

In some embodiments of any of the embodiments described herein, m is in a range of from 0 to 50. In some such embodiments, n is in a range of from 2 to 1,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

In some embodiments of any of the embodiments described herein, m is in a range of from 0 to 20. In some such embodiments, n is in a range of from 2 to 1,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

In some embodiments of any of the embodiments described herein, m is in a range of from 0 to 10. In some such embodiments, n is in a range of from 2 to 1,000. In some such embodiments, n is in a range of from 3 to 1,000. In some embodiments, n is in a range of from 3 to 500. In some embodiments, n is in a range of from 3 to 200. In some embodiments, n is in a range of from 3 to 100. In some embodiments, n is in a range of from 3 to 50. In some embodiments, n is in a range of from 5 to 50. In some embodiments, n is in a range of from 10 to 50.

Lipid Moiety:

The lipid moiety (represented by the variable X in formula I herein) according to any of the embodiments in this section may be attached to a polymeric moiety according to any of the embodiments described in the section herein relating to the polymeric moiety.

The lipid moiety may optionally be derived from any lipid known in the art (including, but not limited to, a naturally occurring lipid). Derivation of the lipid moiety from the lipid may optionally consist of substituting a hydrogen atom at any position of the lipid with the polymeric moiety represented in general formula I by [Y(-L-Z)]n[Y]m (i.e., the polymeric moiety represented by general formula Ia).

In some embodiments of any of the embodiments described herein, the lipid moiety (according to any of the respective embodiments described herein) is attached to a Y(-L-Z) unit (according to any of the embodiments described herein relating to Y, L and/or Z), that is, backbone unit substituted by the pendant group described herein (e.g., rather than a backbone unit not substituted by the pendant group).

Alternatively or additionally, in some embodiments of any of the embodiments described herein wherein m is at least 1, the lipid moiety (according to any of the respective embodiments described herein) may optionally be attached to a backbone unit (Y) which is not substituted by a pendant group described herein (e.g., rather than attached to a backbone unit substituted by the pendant group). For example, the polymeric moiety may optionally be a copolymer wherein the identity of the backbone unit attached to the lipid moiety varies randomly between molecules. Thus, the depiction of X in Formula I as being attached to a backbone unit substituted by a pendant group (i.e., Y-(L-Z)) rather than to an unsubstituted backbone unit Y is arbitrary, and is not intended to be limiting.

In some embodiments of any of the embodiments described herein, the lipid moiety is a moiety of a lipid which is a fatty acid, a monoglyceride, a diglyceride, a triglyceride, a glycerophospholipid, a sphingolipid, or a sterol. In some embodiments, the lipid is a glycerophospholipid.

In some embodiments of any of the embodiments described herein, the lipid moiety comprises at least one fatty acid moiety (e.g., an acyl group derived from a fatty acid). The fatty acid moiety may be derived from a saturated or unsaturated fatty acid. For example, the lipid moiety may consist of a fatty acid moiety, or be a monoglyceride moiety comprising one fatty acid moiety, a diglyceride moiety comprising two fatty acid moieties, or a triglyceride moiety comprising three fatty acid moieties.

Examples of fatty acid moieties which may optionally be comprised by the lipid moiety include, without limitation, lauroyl, myristoyl, palmitoyl, stearoyl, palmitoleoyl, oleoyl, and linoleoyl.

Suitable examples of glycerophospholipids include, without limitation, a phosphatidyl ethanolamine, a phosphatidyl serine, a phosphatidyl glycerol and a phosphatidyl inositol.

In some embodiments of any of the embodiments described herein, the lipid moiety represented by the variable X has the general formula III:

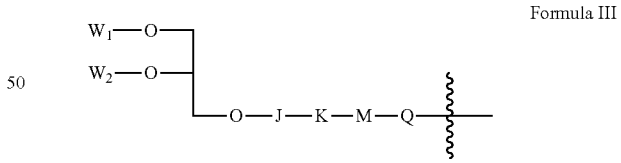

Formula III $W_1$ and $W_2$ are each independently hydrogen, alkyl, alkenyl, alkynyl or acyl, wherein at least one of $W_1$ and $W_2$ is not hydrogen;

J is —P(=O)(OH)—O—, or J is absent (such that K is attached directly to the depicted oxygen atom of a glycerol moiety);

K is a substituted or unsubstituted hydrocarbon from 1 to 10 carbon atoms in length;

M is a linking group which is —O—, —S—, amino, sulfinyl, sulfonyl, phosphate, phosphonyl, phosphinyl, carbonyl, thiocarbonyl, urea, thiourea, carbamyl, thiocarbamyl, amido, carboxy, or sulfonamide, or M is absent (such that K is attached directly to Q); and Q is a substituted or unsubstituted hydrocarbon from 1 to 10 carbon atoms in length, or Q is absent.

Q is attached to a backbone unit of the polymeric backbone according to any of the respective embodiments described herein, or alternatively, when Q is absent, M is attached to the aforementioned backbone unit.

When M is absent, Q is also absent, and K is attached to a backbone unit of the polymeric backbone according to any of the respective embodiments described herein.

In some embodiments of any of the embodiments described herein, one of $W_1$ and $W_2$ is hydrogen and the other is not hydrogen.

In some embodiments of any of the embodiments described herein, neither $W_1$ nor $W_2$ is hydrogen.

In some embodiments of any of the embodiments described herein, at least one of $W_1$ and $W_2$ is an alkyl, alkenyl, alkynyl or acyl, which is from 10 to 30 carbon atoms in length. In some embodiments, each of $W_1$ and $W_2$ is from 10 to 30 carbon atoms in length.

Examples of acyl groups which may optionally serve independently as $W_1$ and/or $W_2$ include, without limitation, lauroyl, myristoyl, palmitoyl, stearoyl, palmitoleoyl, oleoyl, and linoleoyl.

In some embodiments of any of the embodiments described herein, J is —P(=O)(OH)—O— (e.g., the lipid moiety is a glycerophospholipid).

Herein, the length of the hydrocarbon represented by the variable K refers to the number of atoms separating J and M (i.e., along the shortest path between J and M) as depicted in formula III.

When K is a substituted hydrocarbon, M may be attached to a carbon atom of the hydrocarbon per se, or be attached to a substituent of the hydrocarbon.

In some embodiments of any of the embodiments described herein, K is an acyl moiety (e.g., —C(=O)—C(CH$_3$)$_2$—). In some such embodiments, J is absent, such that K is attached directly to the depicted oxygen atom of a glycerol moiety. In some such embodiments, K comprises a carbonyl linking group (—C(=O)—), which attaches to the oxygen atom of a glycerol moiety via an ester bond.

In some embodiments of any of the embodiments described herein, K is an ethanolamine moiety (e.g., —CH$_2$—CH$_2$—NH—, or —CH$_2$—CH$_2$— attached to a nitrogen atom), a serine moiety (e.g., —CH$_2$—CH(CO$_2$H)—NH—, or —CH$_2$—CH(CO$_2$H)— attached to a nitrogen atom), a glycerol moiety (e.g., —CH(OH)—CH(OH)—CH—O—) and an inositol moiety (e.g., -cyclohexyl(OH)$_4$—O—). In some embodiments, J is —P(=O)(OH)—O—.

In some embodiments of any of the embodiments described herein, M is amido, optionally —C(=O)NH—.

In some embodiments, the nitrogen atom of the amido is attached to K. In some such embodiments, K is an ethanolamine or serine moiety described herein.

In some embodiments of any of the embodiments described herein, Q is a substituted or unsubstituted methylene group. In some such embodiments, M is amido. In some embodiments, the C(=O) of the amido is attached to Q.

In some embodiments of any of the embodiments described herein, Q is a methylene group substituted by one or two substituents. In some embodiments, the methylene group is substituted by one or two alkyl groups (e.g., $C_{1-4}$-alkyl).

In some embodiments of any of the embodiments described herein, Q is a methylene group substituted by two substituents. In some embodiments, the methylene group is substituted by two alkyl groups (e.g., $C_{1-4}$-alkyl). In some embodiments, the alkyl groups are methyl, such that Q is dimethylmethylene (—C(CH$_3$)$_2$—).

As exemplified in the Examples section herein, a substituted methylene (e.g., di-substituted methylene) represented by the variable Q is particularly suitable for participating in polymerization reactions (e.g., as an initiator), because a free radical and/or ion on the methylene may be stabilized by the substituent(s) thereof.

As further exemplified herein, formation of an amido group (represented by the variable M) may serve as a convenient way to attach the abovementioned substituted methylene to a lipid (e.g., a naturally occurring lipid) such as a phosphatidylethanolamine or phosphatidylserine.

In some embodiments of any of the embodiments described herein, M and Q are each absent, and K is terminated by a substituted or unsubstituted methylene group, according to any of the respective embodiments described herein with respect to Q, for example, a methylene group substituted by two substituents (e.g., dimethylmethylene (—C(CH$_3$)$_2$—)). In some embodiments, K further comprises a carbonyl group according to any of the respective embodiments described herein.

In some embodiments of any of the embodiments described herein, J, M and Q are each absent. In some such embodiments, K comprises a carbonyl linking group (—C(=O)—) attached directly to the depicted oxygen atom of a glycerol moiety (via an ester bond), and further comprises a substituted or unsubstituted methylene group (e.g., dimethylmethylene). In some embodiment, K consists of a carbonyl linking group attached directly to the depicted oxygen atom of a glycerol moiety (via an ester bond), and a substituted or unsubstituted methylene group, for example, K is —C(=O)—C(CH$_3$)$_2$—.

Targeting Moiety:

As described hereinabove, in some embodiments of any of the embodiments described herein, at least a portion of the monomeric units comprise a targeting moiety (according to any of the embodiments described herein relating to a targeting moiety).

Herein, a "targeting moiety" refers to a moiety which is capable of bringing a compound (e.g., a compound according to some embodiments of the invention) into proximity with a selected substance and/or material (which is referred to herein as a "target"). The target is optionally a cell (e.g., a proliferating cell associated with the proliferative disease or disorder), wherein the proximity is such that the targeting moiety facilitates attachment and/or internalization of the compound into a target cell, and such that the compound may exert a therapeutic effect.

In any of the embodiments described herein wherein m is at least 1, at least a portion of the monomeric units comprising a targeting moiety (the number of which is represented by the variable m), according to any of the respective embodiments described herein, are monomeric units which do not comprise the pendant group represented by (-L-Z). In some such embodiments, each of the monomeric units comprising a targeting moiety (according to any of the respective embodiments described herein) is a monomeric unit which comprises the pendant group represented by (-L-Z) (i.e., a backbone unit Y substituted by (-L-Z)), that is, none of the monomeric units comprising the pendant group represented by (-L-Z) comprise the aforementioned targeting moiety.

In any of the embodiments described herein wherein m is at least 1, each of the monomeric units which do not comprise the pendant group represented by (-L-Z) (the number of which is represented by the variable m) comprises a targeting moiety (according to any of the respective embodiments described herein). In some such embodiments, each of the monomeric units comprising a targeting moiety (according to any of the respective embodiments described herein) is a monomeric unit which does not comprise the pendant group represented by (-L-Z), that is, none of the monomeric units comprising the pendant group represented by (-L-Z) comprise the aforementioned targeting moiety, and each of the monomeric units which does not comprise the pendant group represented by (-L-Z) comprises the aforementioned targeting moiety.

In any of the embodiments described herein wherein m is at least 1, a monomeric unit comprising a targeting moiety may consist essentially of a backbone unit Y (according to any of the respective embodiments described herein) substituted by one or more targeting moieties (according to any of the respective embodiments described herein).

The backbone unit Y of a monomeric unit comprising a targeting moiety may optionally be different (optionally considerably different) in structure than a backbone unit Y of other monomeric units in the polymeric moiety (according to any of the respective embodiments described herein).

In any of the embodiments described herein wherein m is at least 1, the polymeric moiety comprises a monomeric unit which comprises a targeting moiety, and said monomeric unit is at a terminus of the polymeric moiety distal to the lipid moiety. In such embodiments, the compound represented by general formula I has the formula Ib:

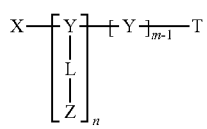

Formula Ib wherein:

T is a monomeric unit comprising a targeting moiety (according to any of the respective embodiments described herein);

X and T are attached to distal termini of the moiety represented by [Y(-L-Z)]n[Y]m−1; and X, Y, L, Z, n and m are defined in accordance with any of the embodiments described herein relating to general formula I, with the proviso that m is at least 1.

It is to be understood that T in formula Ib is a type of monomeric unit represented by Y (i.e., without the pendant group represented by (-L-Z)) in formulas I and Ia, and the number of monomeric units represented by Y (i.e., without the pendant group represented by (-L-Z)) other than T is represented by the value m−1, such that the total number of monomeric units without the pendant group represented by (-L-Z)), including T, is represented by the variable m, as in formulas I and Ia.

In some embodiments, m is 1, such that m−1 is zero, and the compound represented by formula Ib consequently has the formula: X—[Y(-L-Z)]n-T, wherein L, T, X, Y, Z and n are defined in accordance with any of the embodiments described herein.

A monomeric unit comprising a targeting moiety according to any of the respective embodiments described herein may optionally be prepared by preparing a monomer comprising a targeting moiety, and using said monomer to prepare a polymeric moiety described herein (e.g., by polymerization of monomers according to any of the respective embodiments described herein) and/or by modifying a monomeric unit in a polymeric moiety subsequently to preparation of a polymeric moiety (e.g., by polymerization of monomers according to any of the respective embodiments described herein), using any suitable technique known in the art, including, but not limited to, techniques for conjugation.

In some embodiments of any of the embodiments described herein relating to a targeting moiety, the targeting moiety does not comprise a moiety having general formula II (according to any of the respective embodiments described herein). For example, even if a moiety represented by general formula II is capable of forming a bond with a target as described herein, the phrase "targeting moiety", in some embodiments, is to be understood as relating to a moiety distinct from a moiety represented by variable Z (having general formula II).

In some embodiments of any one of the embodiments described herein, the pendant group represented by (-L-Z) is selected so as not to form a bond with the target and/or so as not to include a structure and/or property of a targeting moiety as described herein in any one of the respective embodiments. For example, in embodiments wherein a targeting moiety comprising a nucleophilic group (according to any of the respective embodiments described herein)—for example, an amine group—is capable of forming a bond (e.g., covalent bond) with a target, the variable Z (having general formula II) is optionally selected such that the depicted amine/ammonium group is a tertiary amine/ammonium (i.e., no more than one of $R_1$-$R_3$ is hydrogen) or quaternary ammonium (i.e., none of $R_1$-$R_3$ is hydrogen), preferably a quaternary ammonium (e.g., comprising a trimethylamino group, such as in phosphocholine). Tertiary amine groups, and especially quaternary ammonium groups, may be significantly less reactive nucleophilic groups than primary and secondary amine groups.

In some embodiments of any of the embodiments described herein relating to a targeting moiety, the targeting moiety comprises (and optionally consists of) at least one functional group capable of forming a covalent bond or non-covalent bond (preferably a selective non-covalent bond) with a substance and/or material (which is referred to herein as a "target"), e.g., at a surface of the target (e.g., a surface of a cell and/or tissue).

Herein, the phrase "functional group" encompasses chemical groups and moieties of any size and any functionality described herein (for example, any functionality capable of forming a covalent bond or non-covalent bond with a target).

A non-covalent bond according to any of the respective embodiments described herein may optionally be effected by non-covalent interactions such as, without limitation, electrostatic attraction, hydrophobic bonds, hydrogen bonds, and aromatic interactions.

In some embodiments, the targeting moiety comprises a functional group capable of forming a non-covalent bond which is selective for the target, e.g., an affinity (e.g., as determined based on a dissociation constant) of the targeting moiety and/or functional group to the target is greater than an affinity of the of the targeting moiety and/or functional group to most (or all) other compounds capable of forming a non-covalent bond with the targeting moiety.

In some embodiments of any one of the embodiments described herein, the functional group(s) are capable of forming a covalent bond with one or more specific functional groups (e.g., hydroxy, amine, thiohydroxy and/or oxo groups) which are present on the target (e.g., a target according to any of the respective embodiments described herein).

Examples of functional groups (in a targeting moiety) capable of forming a covalent bond with a target (according to any of the respective embodiments described herein) and the type of covalent bonds they are capable of forming, include, without limitation:

nucleophilic groups such as thiohydroxy, amine (e.g., primary or secondary amine) and hydroxy, which may form covalent bonds with, e.g., a nucleophilic leaving group (e.g., any nucleophilic group described herein), Michael acceptor (e.g., any Michael acceptor described herein), acyl halide, isocyanate and/or isothiocyanate (e.g., as described herein) in a target;

nucleophilic leaving groups such as halo, azide (—$N_3$), sulfate, phosphate, sulfonyl (e.g. mesyl, tosyl), N-hydroxysuccinimide (NHS) (e.g. NHS esters), sulfo-N-hydroxysuccinimide, and anhydride, which may form covalent bonds with, e.g., a nucleophilic group (e.g., as described herein) in a target;

Michael acceptors such as enones (e.g., maleimide, acrylate, methacrylate, acrylamide, methacrylamide), nitro groups and vinyl sulfone, which may form covalent bonds with, e.g., a nucleophilic group (e.g., as described herein) in a target, optionally thiohydroxy;

dihydroxyphenyl groups (according to any of the respective embodiments described herein), which may form covalent bonds with, e.g., a nucleophilic group (e.g., as described herein) and/or a substituted or unsubstituted phenyl group (e.g., another dihydroxyphenyl group) in a target, as described herein;

an acyl halide (—C(=O)-halogen), isocyanate (—NCO) and isothiocyanate (—N=C=S) group, which may form covalent bonds with, e.g., a nucleophilic group (e.g., as described herein) in a target;

a carboxylate (—C(=O)OH) group, which may form a covalent bond with, e.g., a hydroxyl group in a target to form an ester bond and/or an amine group (e.g., primary amine) in a target to form an amide bond (optionally by reaction with a coupling reagent such as a carbodiimide); and/or a carboxylate group is in a target and may form an amide or ester bond with an amine or hydroxyl group, respectively, in the targeting moiety;

an oxo group (optionally in an aldehyde group (—C(=O)H)), which may form a covalent imine bond with an amine group (e.g., a primary amine) in a target; and/or an oxo group (optionally in an aldehyde group) is in a target and may form a covalent imine bond with an amine groups in the targeting moiety; and/or thiohydroxy groups, which may form covalent disulfide (—S—S—) bonds with a thiohydroxy group in a target.

Modification of a monomer (e.g., prior to polymerization) or a monomeric unit of a polymeric moiety (e.g., subsequent to polymerization) to comprise any of the functional groups described herein may optionally be performed using any suitable technique for conjugation known in the art. The skilled person will be readily capable of selecting a suitable technique for any given molecule to be modified.

Herein, the term "dihydroxyphenyl" refers to an aryl group (as defined herein) which is a phenyl substituted by two hydroxyl groups at any positions thereof. The phenyl may optionally be substituted by additional substituents (which may optionally comprise additional hydroxyl groups), to thereby form a substituted dihydroxyphenyl group; or alternatively, the phenyl comprises no substituents other than the two hydroxyl groups, such that the dihydroxyphenyl group is an unsubstituted dihydroxyphenyl group.

In some embodiments of any one of the embodiments described herein, the dihydroxyphenyl group is an ortho-dihydroxyphenyl (wherein the hydroxyl groups are attached to the phenyl at adjacent positions) or a para-dihydroxyphenyl (wherein the hydroxyl groups are attached to opposite sides of the phenyl ring), each being a substituted or unsubstituted dihydroxyphenyl. In some such embodiments, the ortho-dihydroxyphenyl or para-dihydroxyphenyl is an unsubstituted dihydroxyphenyl.

A dihydroxyphenyl group according to any of the respective embodiments described herein may optionally bond covalently and/or non-covalently to a target according to any one or more attachment mechanism described for dihydroxyphenyl (catechol) groups in Lee et al. [*PNAS* 2006, 103:12999-13003], Brodie et al. [*Biomedical Materials* 2011, 6:015014] and/or International Patent Application PCT/IL2015/050606, the contents of each of which are incorporated in their entirety, and especially contents regarding bonds formed by dihydroxyphenyl (catechol) groups to surfaces.

In some embodiments of any one of the embodiments described herein, the functional group capable of forming a bond to a target is a functional group capable of forming a covalent bond with an amine group, optionally a primary amine group. In some such embodiments, the target comprises on or more amino acids or amino acid residues, for example, a peptide or polypeptide of any length (e.g., at least two amino acid residues, for example, proteins), and the amine groups may optionally be lysine side chain amine groups and/or N-terminal amine groups. In some embodiments, the target comprises an extracellular matrix protein, for example, collagen. In some embodiments, the target comprises cartilage (e.g., articular cartilage).

In some embodiments of any one of the embodiments described herein, the targeting moiety comprises (and optionally consists of) at least one functional group capable of forming a non-covalent bond with the target (e.g., as described herein in any one of the respective embodiments).

In some embodiments of any one of the embodiments described herein, a functional group capable of forming a non-covalent bond with the target comprises (and optionally consists of) a polysaccharide and/or polypeptide (e.g., a protein and/or fragment thereof), wherein the target optionally comprises a ligand of the polysaccharide and/or polypeptide; and/or the target comprises a polysaccharide and/or polypeptide (e.g., a protein and/or fragment thereof) and the functional group capable of forming a non-covalent bond with the target is a ligand of the polysaccharide and/or polypeptide.

Examples of suitable polysaccharides and/or polypeptides, and ligands thereof, include, without limitation:

avidin or streptavidin as a polypeptide described herein, and biotin as a ligand thereof;

a polysaccharide-binding polypeptide as a polypeptide described therein, and a complementary polysaccharide as a ligand thereof (or a complementary polysaccharide-binding polypeptide as a ligand of a polysaccharide described herein);

a collagen-binding polypeptide as a polypeptide described therein, and a complementary collagen as a ligand thereof (or a collagen as a polypeptide described herein and a complementary collagen-binding polypeptide as a ligand thereof);

a cell receptor expressed by a cell, and a ligand selectively bound by the receptor;

an antibody towards any antigen (e.g., wherein the target described herein optionally comprises the antigen) or a fragment of such an antibody as a polypeptide described herein, and the respective antigen as a ligand thereof; and an antibody mimetic towards any antigen (e.g., wherein the target described herein optionally comprises the antigen).

Examples of cell receptors expressed by a cell include, without limitation, receptors characteristic of a particular type of cell and/or tissue, and receptors overexpressed by a cancer cell. The cell receptor or the cell is optionally a target described herein, and the targeting moiety optionally comprises any ligand of the receptor. Examples of such ligands include, without limitation, transferrin, a ligand of transferrin receptor which may optionally target transferrin receptor overexpressed by some cancer cells; keratinocyte growth factor (KGF or FGF7) which is specific for cells of epithelial origin, and may optionally target KGF receptor such as that overexpressed by an endometrial carcinoma or pancreatic carcinoma [Visco et al., *Int J Oncol* 1999, 15:431-435; Siegfried et al., *Cancer* 1997, 79:1166-1171]; and epidermal growth factor (EGF) which may optionally target an EGF receptor, optionally an erbB, such as that overexpressed by gliomas and endometrial carcinomas [Normanno et al., *Curr Drug Targets* 2005, 6:243-257]).

As used herein, the term "antibody" encompasses any type of immunoglobin. As used herein, the phrase "antibody mimetic" encompasses any type of molecule, optionally a polypeptide, referred as such in the art capable of selectively binding an antigen (e.g., non-covalently). Non-limiting examples of antibody mimetics include affibodies, affilins, affimers, affitins, alphabodies, anticalins, avimers, DARPins, Fynomers, Kunitz domain peptides, and monobodies, e.g., as described in Nygren [*FEBS J* 2008, 275: 2668-2676], Ebersbach et al. [*J Mol Biol* 2007, 372:172-185], Johnson et al. [*Anal Chem* 2012, 84:6553-6560], Krehenbrink et al. [*J Mol Biol* 2008, 383:1058-1068], Desmet et al. [*Nature Comm* 2014, 5:5237], Skerra [*FEBS J* 2008, 275:2677-2683], Silverman et al. [*Nature Biotechnol* 2005, 23:1556-1561], Stumpp et al. [*Drug Discov Today* 2008, 13:695-701], Grabulovski et al. [*J Biol Chem* 2007, 282:3196-3204], Nixon & Wood [*Curr Opin Drug Discov Devel* 2006, 9:261-268], Koide & Koide [*Methods Mol Biol* 2007, 325:95-109], and Gebauer & Skerra [*Curr Opin Chem Biol* 2009, 13:245-255], the contents of each of which are incorporated in their entirety, and especially contents regarding particular types of antibody mimetics.

As used herein, the phrase "polysaccharide-binding polypeptide" encompasses any polypeptide or oligopeptide (peptide chains of at least 2, and preferably at least 4 amino acid residues in length) capable of selectively binding (e.g., non-covalently) to a polysaccharide. A wide variety of polysaccharide-binding polypeptides and their binding specificities will be known to the skilled person, and include short peptide sequences (e.g., from 4 to 50, optionally 4 to 20 amino acid residues in length), and longer polypeptides such as proteins or fragments (e.g., carbohydrate-binding modules and/or domains) thereof. In addition, the phrase "polysaccharide-binding polypeptide" encompasses antibodies capable of specifically binding to a polysaccharide. Such antibodies will be available to the skilled person and/or the skilled person will know how to prepare such antibodies, using immunological techniques known in the art.

Examples of polysaccharide-binding polypeptides which may be used in some of any one of the embodiments of the invention include, without limitation, carbohydrate-binding modules (CBMs); and hyaluronic acid-binding peptides, polypeptides and/or modules (e.g., having a sequence as described in any of International Patent Application publication WO 2013/110056; International Patent Application publication WO 2014/071132; Barta et al. [*Biochem J* 1993, 292:947-949], Kohda et al. [*Cell* 1996, 86:767-775], Brisset & Perkins [*FEBS Lett* 1996, 388:211-216], Peach et al. [*J Cell Biol* 1993, 122:257-264], Singh et al. [*Nature Materials* 2014, 13:988-995], and Zaleski et al. [*Antimicrob Agents Chemother* 2006, 50:3856-3860], the contents of each of which are incorporated in their entirety, and especially contents regarding particular polysaccharide-binding polypeptides), for example, GAHWQFNALTVR (a hyaluronic acid-binding peptide sequence).

Examples of CBMs which may be used in some of any one of the embodiments of the invention, include, without limitation, CBMs belonging to the families CBM3, CBM4, CBM9, CBM10, CBM17 and/or CBM28 (which may optionally be used to bind cellulose, e.g., in a cellulose-containing target); CBM5, CBM12, CBM14, CBM18, CBM19 and/or CBM33 (which may optionally be used to bind chitin and/or other polysaccharides comprising N-acetylglucosamine, e.g., in a chitin-containing target); CBM15 (which may optionally be used to bind hemicellulose, e.g., in a hemicellulose-containing target); and/or CBM20, CBM21 and/or CBM48 (which may optionally be used to bind starch and/or glycogen, e.g., in a starch-containing and/or glycogen-containing target).

As used herein, the phrase "collagen-binding polypeptide" encompasses any polypeptide or oligopeptide (peptide chains of at least 2, and preferably at least 4 amino acid residues in length) capable of selectively binding (e.g., non-covalently) to a collagen (e.g., one type of collagen, some types of collagen, all types of collagen), including glycosylated polypeptides and oligopeptides such as peptidoglycans and proteoglycans. A wide variety of collagen-binding polypeptides and their binding specificities will be known to the skilled person, and include short peptide sequences (e.g., from 4 to 50, optionally 4 to 20 amino acid residues in length), and longer polypeptides such as proteins or fragments (e.g., collagen-binding domains) thereof. In addition, the phrase "collagen-binding polypeptide" encompasses antibodies capable of specifically binding to a collagen. Such antibodies will be available to the skilled person and/or the skilled person will know how to prepare such antibodies, using immunological techniques known in the art.

Examples of collagen-binding polypeptides which may be used in embodiments of the invention include, without limitation, collagen-binding proteins (e.g., decorin), fragments thereof and/or other polypeptides as described in U.S. Pat. No. 8,440,618, Abd-Elgaliel & Tung [Biopolymers 2013, 100:167-173], Paderi et al. [*Tissue Eng Part A* 2009, 15:2991-2999], Rothenfluh et al. [*Nat Mater* 2008, 7:248-254] and Helms et al. [*J Am Chem Soc* 2009, 131:11683-11685] (the contents of each of which are incorporated in their entirety, and especially contents regarding particular collagen-binding polypeptides), for example, the sequence WYRGRL.

It is expected that during the life of a patent maturing from this application many relevant functional groups and moieties for binding will be developed and/or uncovered and the scope of the terms "targeting moiety", "functional group", "cell receptor", "antibody", "antibody mimetic", "collagen-binding polypeptide" and "polysaccharide-binding polypeptide" and the like is intended to include all such new technologies a priori.

In some embodiments of any of the embodiments described herein, a functional group in a targeting moiety (according to any of the respective embodiments described herein) is attached to a linking group (as defined herein). The linking group may optionally be any linking group or linking moiety described herein, including, without limitation, a substituted or unsubstituted hydrocarbon. In some embodiments, the targeting moiety (optionally a substituent of a backbone unit Y) consists essentially of a functional group attached to the rest of the polymeric moiety via the linking group.

A functional group may optionally be attached to the linking moiety by a covalent bond obtainable by a reaction between two functional groups, for example, any covalent bond and/or functional groups described herein in the context of forming a covalent bond between a functional group and a target.

In some embodiments of any of the embodiments described herein relating to a functional group comprising a peptide or polypeptide, an amino acid residue of the peptide or polypeptide is optionally attached to a linking group of the targeting moiety, for example, via an amide bond formed from an amine or carboxylate group in the peptide or polypeptide (e.g., in an N-terminus, a lysine side chain, a C-terminus, a glutamate side chain and/or an aspartate side chain), an ester bond formed from a hydroxyl or carboxylate group in the peptide or polypeptide (e.g., in a serine side chain, a threonine side chain, a C-terminus, a glutamate side chain and/or an aspartate side chain), and/or a disulfide bond formed from a thiohydroxy group in the peptide or polypeptide (e.g., in a cysteine side chain). In some embodiments, an amino acid residue attached to the linking group is an N-terminal and/or C-terminal residue, for example, any amino acid residue attached via an N-terminal amino group or C-terminal carboxylate group, and/or a terminal lysine, glutamate, aspartate, serine, threonine and/or cysteine residue attached via a side chain thereof.

In some embodiments, an amino acid residue and/or peptide (e.g., from 2 to 20 amino acid residues in length) is added to the N-terminus and/or C-terminus of a peptide or polypeptide sequence of a functional group (according to any of the respective embodiments described herein), and links the aforementioned sequence to a linking group. Examples of such terminal amino acid residues and/or peptides include, without limitation, glycine residues and peptides with a terminal glycine residue, which may be used to attach a linking group to an N-terminus or C-terminus (according to any of the respective embodiments described herein); serine and threonine residues and peptides with a terminal serine or threonine residue, which may be used to attach a linking group to hydroxyl group in a serine or threonine side chain, optionally via an ester bond (according to any of the respective embodiments described herein); and cysteine residues and peptides with a terminal cysteine residue, which may be used to attach a linking group to a peptide via a disulfide bond (according to any of the respective embodiments described herein).

In some embodiments, attachment of a peptide or polypeptide to a linking group via a terminal amino acid residue minimizes interference (e.g., steric interference) with the functionality of the peptide or polypeptide following attachment to the linking group.

In some embodiments, attachment of a peptide or polypeptide to a linking group via a terminal glycine facilitates attachment by minimizing interference (e.g., steric interference) of an amino acid side chain (which glycine lacks) with attachment to the linking group.

Lipid Layers and Liposomes:

According to an aspect of some embodiments of the invention, there is provided a lipid bilayer (referred to herein interchangeably as simply a "bilayer") comprising a polymeric compound according to any of the respective embodiments described herein. In some such embodiments, the bilayer further comprises at least one bilayer-forming lipid in addition to the polymeric compound.

Herein, the term "bilayer-forming lipid" encompasses any compound in which a bilayer may form from a pure aqueous solution of the compound, the bilayer comprising two parallel layers of molecules of the compound (referred to as a "lipid").

Typically, the bilayer comprises relatively polar moieties of the lipid at the two surfaces of the bilayer, which may optionally comprise an interface with the aqueous solution and/or an interface with a solid surface; and relatively hydrophobic moieties of the lipid at the interior of the bilayer, at an interface between the two layers of lipid molecules which form the bilayer.

Examples of bilayer-forming lipids include glycerophospholipids (e.g., a glycerophospholipid according to any of the respective embodiments described herein). It is to be appreciated that the polymeric compound described herein may optionally be a bilayer-forming lipid which can form a bilayer per se or in combination with one or more additional bilayer-forming lipids.

In some embodiments of any one of the embodiments described herein, the bilayer-forming lipid comprises at least one charged group (e.g., one or more negatively charged groups and/or one or more positively charged groups).

In some embodiments, the bilayer-forming lipid is zwitterionic; comprising both (e.g., an equal number of) negatively charged and positively charged groups (e.g., one of each).

In some embodiments of any of the embodiments described herein relating to a bilayer, a molar ratio of the bilayer-forming lipid (comprised in addition to the polymeric compound) and the polymeric compound in the bilayer is in a range of from 5:1 to 5,000:1 (bilayer-forming lipid:polymeric compound), optionally in a range of from 10:1 to 2,500:1, optionally in a range of from 25:1 to 1,000:1, and optionally in a range of from 50:1 to 500:1.

In some embodiments of any of the embodiments described herein relating to a bilayer, a polymeric moiety in the bilayer comprises a lipid moiety represented by the variable X in formula I (according to any of the respective embodiments described herein) which comprises a residue of a bilayer-forming lipid (e.g., a glycerophospholipid) which is comprised by the bilayer in addition to the polymeric moiety or which is closely related to a bilayer-forming lipid comprises by the bilayer, for example, wherein the lipid moiety comprises a glycerophospholipid residue and the bilayer comprises another glycerophospholipid as a bilayer-forming lipid (e.g., optionally wherein fatty acid residues in the glycerophospholipid residue have about the same length as fatty acid residues in the bilayer-forming lipid, and optionally wherein the fatty acid residues in the glycerophospholipid residue are substantially the same as the fatty acid residues in the bilayer-forming lipid).

Without being bound by any particular theory, it is believed that similarity between a lipid moiety of a polymeric moiety and a bilayer-forming lipid facilitates anchorage of the lipid moiety of the polymeric moiety in a bilayer comprising the bilayer-forming lipid.

The bilayer according to embodiments described herein may optionally be closed upon itself (e.g., such that the bilayer has no edges), thereby forming an inner volume separated by the bilayer from the surrounding environment, which is referred to herein and in the art as a "liposome". Alternatively or additionally, the bilayer may be open-faced and/or with edges.

According to an aspect of some embodiments of the invention, there is provided a liposome comprising at least one lipid bilayer according to any of the respective embodiments described herein.

A liposome may optionally comprise a single bilayer or a plurality of bilayers (each bilayer optionally independently forming a closed vesicle) comprising, for example, concentric bilayer vesicles and/or a plurality of separate bilayer vesicles encompassed by the same bilayer vesicle.

A liposome according to any of the respective embodiments described herein may be approximately spherical in shape or may have any alternative shape, such as an elongated tube and/or a flattened (e.g., sheet-like) shape.

In some embodiments of any of the embodiments described herein relating to a liposome, the liposome further comprises at least one functional moiety or agent bound to a surface of the liposome and/or within a lipid bilayer and/or core of the liposome (e.g., within the liposome bilayer and/or enveloped by the liposome bilayer).

Examples of functional moieties and agents suitable for inclusion in embodiments described herein include, without limitation, a therapeutically active agent or moiety of a therapeutically active agent (e.g., wherein the active agent is releasable upon cleavage of the moiety), a labeling moiety or agent, and/or a targeting moiety or targeting agent (e.g., a targeting moiety or agent on a surface of the liposome).

Examples of therapeutically active agents suitable for inclusion in a liposome (e.g., as a molecule or moiety of the agent) include, without limitation, amphotericin B, cisplatin, cytarabine, daunorubicin, doxorubicin, estradiol, influenza virosome, morphine, surfactant protein B, surfactant protein C, verteporfin and vincristine.

Examples of a labeling moiety or agent include moieties and compounds which are chromophoric (e.g., absorb visible light), fluorescent, phosphorescent, and/or radioactive. Many such compounds and moieties (and techniques for preparing such moieties) will be known to a skilled person.

A targeting moiety in a liposome according to any of the respective embodiments described herein may optionally be a targeting moiety according to any of the respective embodiments described herein. A targeting moiety in a liposome may be comprised by a polymeric compound according to some embodiments of the invention (according to any of the respective embodiments described herein), the liposome comprising the polymeric compound. Alternatively or additionally, a targeting moiety in a liposome may optionally be comprised by another compound in the liposome, optionally a bilayer-forming lipid (according to any of the respective embodiments described herein) conjugated to a targeting moiety according to any of the respective embodiments described herein.

Herein, a "targeting agent" refers to a compound ("agent") comprising (and optionally consisting essentially of) a targeting moiety according to any of the respective embodiments described herein (e.g., in the context of a targeting moiety comprised by a polymeric compound described herein). Typically, the phrase "targeting agent" is used to refer to a compound other than a polymeric compound comprising a targeting moiety, as described herein.

In some embodiments, a functional moiety (e.g., targeting moiety or labeling moiety) is covalently attached to a liposome. Such attachment may be obtained in some embodiments by using techniques known in the art (e.g., amide bond formation).

According to another aspect of embodiments of the invention, there is provided a composition-of-matter comprising a substrate coated, on at least a portion of a surface thereof, by at lipid bilayer according to any of the respective embodiments described herein.

According to another aspect of embodiments of the invention, there is provided an article of manufacture comprising a composition-of-matter according to any one of the embodiments described herein.

Herein, the term "composition-of-matter" refers to any composition comprising a plurality of substances (e.g., substrate, water-soluble polymer(s), and amphiphilic lipid) in a form which does not exist in nature, and which does not include a portion of a human being. The form which does not exist in nature may optionally comprise natural substances in a combination which does not exist in nature, and/or may optionally comprise one or more substances which do not occur in nature. It is to be understood that this definition is not necessarily identical with a standard legal definition of the term.

Herein, the term "article of manufacture" refers to any article produced from materials in a manner which results in new forms, qualities, properties or combinations of the materials. It is to be understood that this definition is not necessarily identical with a standard legal definition of the term. The article of manufacture described herein may optionally consist essentially of the composition-of-matter, or alternatively, may comprise additional materials and/or parts.

At least a portion of the molecules of the amphiphilic lipid are oriented such that polar groups thereof (e.g., charged groups) face outwards at a surface of the composition-of-matter.

As used herein, the phrase "face outwards at a surface" refers to a group in a molecule (e.g., a lipid) which is closer to the surface of the composition-of-matter than the center of gravity of the molecule is to the surface of the composition-of-matter, and farther from the substrate than the center of gravity of the molecule is from the substrate.

As discussed herein, and without being bound by any particular theory, it is believed that outwards facing polar groups (e.g., charged groups) according to some embodiments of the invention are effect highly effective lubrication and/or inhibition of adhesion, biofouling and/or biofilm formation (e.g., as described herein) due, at least in part, to properties of hydrated polar groups (e.g., hydration lubrication), especially hydrated charged groups.

In any of the embodiments described herein, the substrate may comprise any type of material or combination of different types of material, including inorganic material and/or organic material, in crystalline, amorphous and/or gel (e.g., hydrogel) forms, for example, metal, mineral, ceramic, glass, polymer (e.g., synthetic polymer, biopolymer), plant and/or animal biomass, and combinations thereof.

In some embodiments, the substrate comprises a physiological surface (e.g., a physiological tissue) and/or a surface in contact with and/or intended to come into contact with a physiological surface (e.g., as described herein in any one of the respective embodiments).

In some embodiments of any of the embodiments described herein, the article is a medical device (the substrate being a medical device or portion of a medical device, as described herein). In some embodiments, the medical device is a device designed to come into contact with a part of the body susceptible to infection, such as an internal portion of the body, a mucous membrane and/or a surface of the eye. Examples of such medical devices include, without limitation, surgical tools and implants (which are for coming into contact with an internal portion of the body) and contact lenses (which are for contacting a surface of the eye).

As used herein throughout, the phrase "medical device" includes any material or device that is used on, in, or through a subject's body, for example, in the course of medical treatment (e.g., for a disease or injury). The subject may be human or a non-human animal, such that the phrase "medical device" encompasses veterinary devices. Medical devices include, but are not limited to, such items as medical implants (including permanent implants and transient implants), wound care devices, medical devices for drug delivery, contact lenses and body cavity and personal protection devices. The medical implants include, but are not limited to, catheters (e.g., urinary catheters, intravascular catheters), injection ports, intubation equipment, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incise drapes. Medical devices for drug delivery include, but are not limited to, needles, drug delivery skin patches, drug delivery mucosal patches and medical sponges. Body cavity and personal protection devices, include, but are not limited to, tampons, sponges, surgical and examination gloves, and toothbrushes. Birth control devices include, but are not limited to, intrauterine devices (IUDs), diaphragms and condoms.

In the context of medical devices, it is to be understood that the medical device is coated by a bilayer described herein, and a bilayer or bilayer-comprising liposome per se is not considered herein to be a medical device.

Exemplary articles include the following:

Medical devices such as, but not limited to, pacemakers, heart valves, replacement joints, catheters, catheter access ports, dialysis tubing, gastric bands, shunts, screw plates, artificial spinal disc replacements, internal implantable defibrillators, cardiac resynchronization therapy devices, implantable cardiac monitors, mitral valve ring repair devices, left ventricular assist devices (LVADs), artificial hearts, implantable infusion pumps, implantable insulin pumps, stents, implantable neurostimulators, maxillofacial implants, dental implants, and the like;

Packages or containers, for example, food packages and containers, beverage packages and containers, medical device packages, agricultural packages and containers (of agrochemicals), blood sample or other biological sample packages and containers, and any other packages or containers of various articles;

Food packages such as packages of dairy products and/or containers for storage or transportation of dairy products;

Milk storage and processing devices such as, but not limited to, containers, storage tanks, raw milk holding equipment, dairy processing operations conveyer belts, tube walls, gaskets, rubber seals, stainless steel coupons, piping systems, filling machine, silo tanks, heat exchangers, post-pasteurization equipment, pumps, valves, separators, and spray devices;

Energy harvesting device, for example, a microelectronic device, a microelectromechanical device, a photovoltaic device and the like;

Microfluidic devices, for example, micro-pumps or micro valves and the like;

Sealing parts, for example, 0 rings, and the like;

Articles having a corrodible surface;

Agricultural devices, as, for example, described herein;

Textiles, for example, tough cottons;

Fuel transportation devices;

Construction elements, such as, but not limited to, paints, walls, windows, door handles, and the like;

Elements of water treatment systems (such as for containing and/or transporting and/or treating aqueous media or water), devices, containers, filters, tubes, solutions and gases and the like; and Elements of organic waste treatment systems (such as for containing and/or disposing and/or transporting and/or treating organic waste), devices, containers, filters, tubes, solutions and gases and the like.

Lubrication:

Liposomes and bilayers described herein may optionally be useful for lubricating a surface, for example, a surface coated by a bilayer described herein, and/or contacted with liposomes described herein.

According to an aspect of some embodiments of the invention, there is provided a lubricant composition comprising liposomes according to any of the respective embodiments described herein.

Herein, a "lubricant composition" refers to a composition intended for reducing a friction coefficient of a surface (e.g., according to a method described herein).

In some embodiments, the lubricant composition comprises a carrier. The carrier may optionally be a liquid carrier. In some embodiments, the carrier comprises an aqueous liquid.

In some embodiments, the lubricant composition (or any other composition descried herein comprising liposomes) further comprises a water-soluble polymer, optionally as part of the carrier.

As used herein, the phrase "water-soluble polymer" encompasses polymers having a solubility of at least 1 gram per liter in an aqueous (e.g., water) environment at pH 7 (at 25° C.).

In some embodiments of any of the embodiments described herein, the water-soluble polymer has a solubility of at least 2 grams per liter (under the abovementioned conditions). In some embodiments, the solubility is at least 5 grams per liter. In some embodiments, the solubility is at least 10 grams per liter. In some embodiments, the solubility is at least 20 grams per liter. In some embodiments, the solubility is at least 50 grams per liter. In some embodiments, the solubility is at least 100 grams per liter.

The water-soluble polymer(s) according to any of the embodiments described herein may comprise at least one ionic polymer and/or at least one non-ionic polymer which are water-soluble as defined herein.

As used herein, the phrase "non-ionic polymer" refers to a polymer which does not have a charged group.

Examples of suitable non-ionic water-soluble polymers include, without limitation, polyvinylpyrrolidone (also referred to herein interchangeably as povidone and/or PVP) and polyethylene oxide (also referred to herein interchangeably as PEO, PEG and/or polyethylene glycol).

As used herein, the phrase "ionic polymer" refers to polymers having at least one charged group, and encompasses polymers having a net negative charge (also referred to herein as "anionic polymers"), polymers having a net positive charge (also referred to herein as "cationic polymers"), and polymers having no net charge (also referred to herein as "zwitterionic polymers"), in an aqueous (e.g., water) environment at pH 7.

Herein throughout, the phrase "charged group" refers to any functional group (e.g., a functional group described herein) which is ionic (as defined herein), including, for example, amine, carboxylic acid, sulfate, sulfonate, phosphate and phosphonate. Thus, each electric charge in a moiety or molecule is associated with one charged group, although a single charged group (e.g., non-substituted phosphate) may be associated with more than one electric charge of the same sign (e.g., a dianion, a dication).

Herein throughout, the term "ionic" refers to the presence of an electric charge on at least one atom in a moiety and/or molecule (in at least 50% of moieties and/or molecules in a population) in an aqueous medium (e.g., water) at pH 7. The electric charge may be negative (anionic) or positive (cationic). If more than one electric charge is present, the electric charges may be negative (anionic) and/or positive (cationic), for example, both a negative and a positive charge may be present (zwitterionic).

Examples of ionic polymers include, without limitation, ionic polysaccharides, such as hyaluronic acid, chondroitin sulfate, alginic acid, xanthan gum, chitosan and N-alkyl chitosan derivatives.

According to another aspect of embodiments described herein, there is provided a method of reducing a friction coefficient of a surface, the method comprising contacting the surface with liposomes according to any of the respective embodiments described herein. In some embodiments, the method is effected by contacting the surface with a composition comprising the liposomes and a carrier (optionally a lubricant composition according to any of the respective embodiments described herein).

In some of any one of the embodiments described herein which relate to a lubrication, according to any one of the aspects described herein, the lubrication is optionally effected according to any of the embodiments described in International Patent Application PCT/IL2015/050605 and/or PCT/IL2015/050606, which are incorporated herein by reference (especially in respect to methods and compositions for lubricating a surface), with the proviso that at least a portion of the liposomes used are in accordance with any of the embodiments described herein.

In some embodiments, the method further comprises contacting the surface with a water-soluble polymer (e.g., according to any of the respective embodiments described herein), optionally prior to and/or concomitantly with contacting the surface with liposomes. In some embodiments, the method is effected by contacting the surface with a composition comprising the liposomes and the water-soluble polymer (optionally a lubricant composition comprising the water-soluble polymer according to any of the respective embodiments described herein), optionally in combination with an aqueous liquid.

In some of any one of the embodiments described herein which relate to a method and/or lubrication composition for reducing a friction coefficient of a surface, the surface is a hydrogel surface. In some embodiments, the hydrogel consists essentially of a polymer and an aqueous liquid (optionally water).

In some of any one of the embodiments described herein which relate to a method and/or lubrication composition for reducing a friction coefficient of a surface, the surface is a contact lens surface.

In some of any one of the embodiments described herein which relate to a contact lens, according to any one of the aspects described herein, the contact lens comprises a hydrogel surface. In some embodiments, the contact lens comprises a hydrogel surface and a rigid center. In some embodiments, the contact lens consists essentially of a hydrogel.

The hydrogel may comprise any material known in the art for use in contact lens hydrogels. Examples of such hydrogel materials include, without limitation, alphafilcon A, asmofilcon A, balafilcon A, bufilcon A, comfilcon A, crofilcon A, deltafilcon A, dimefilcon, droxifilcon A, enfilcon A, etafilcon A, galyfilcon A, hefilcon A, hefilcon B, hilafilcon A, hilafilcon B, hioxifilcon A, hioxifilcon D, isofilcon, lidofilcon A, lidofilcon B, lotrafilcon B, mafilcon, methafilcon A, methafilcon B, narafilcon A, narafilcon B, ocufilcon A, ocufilcon B, ofilcon A, omafilcon A, perfilcon, phemfilcon A, polymacon, scafilcon A, senofilcon A, surfilcon, tefilcon, tetrafilcon A, tetrafilcon B, vifilcon A, and xylofilcon A.

In some embodiments of any one of the embodiments described herein, the hydrogel comprises a polymer consisting of poly(2-hydroxyethyl methacrylate) and/or a silicone. In some embodiments, the polymer comprises a silicone. Such polymers may optionally comprise small amounts of additional monomers (e.g., cross-linking monomers) copolymerized with the 2-hydroxyethyl methacrylate or silicone monomer. For example, 2-hydroxyethyl methacrylate may optionally be copolymerized with vinyl pyrrolidone, methyl methacrylate, methacrylic acid (an anionic monomer), ethylene glycol dimethacrylate (a cross-linking monomer) and/or 3-(ethyldimethyl-ammonium)propyl methacrylamide (a cationic monomer) in a contact lens hydrogel.

Physiological Surfaces:

In some embodiments of any of the embodiments described herein relating to a method and/or lubrication composition for reducing a friction coefficient of a surface, the surface is a physiological surface, and a carrier used with the liposomes (e.g., in a lubricant composition according to any of the respective embodiments described herein) is a physiologically acceptable carrier.

In some embodiments, a surface for which a friction coefficient is reduced according any of the respective embodiments described herein is an articular surface of a synovial joint.

In some embodiments, the method of reducing a friction coefficient of a surface is for use in the treatment of a synovial joint disorder associated with an increased friction coefficient of an articular surface in the synovial joint.

In some embodiments of any of the embodiments described herein relating to a liposome, the liposome is for use in the treatment of a synovial joint disorder associated with an increased friction coefficient of an articular surface in the synovial joint.

According to another aspect of embodiments described herein, there is provided a use of a liposome according to any of the respective embodiments described herein in the manufacture of a medicament for treating a synovial joint disorder associated with an increased friction coefficient of an articular surface in the synovial joint.

Examples of synovial joint disorders associated with an increased friction coefficient of an articular surface, and treatable according to embodiments of various aspects of the invention, include, without limitation, arthritis, traumatic joint injury, locked joint (also known in the art as joint locking), and joint injury associated with surgery.

In some embodiments, the arthritis is osteoarthritis, rheumatoid arthritis and/or psoriatic arthritis.

In some embodiments, the locked joint is associated with osteochondritis dissecans and/or synovial osteochondromatosis.

The joint injury associated with surgery described herein may optionally be associated with surgery which directly inflicts damage on an articular surface (e.g., by incision), and/or surgery which damages an articular surface only indirectly. For example, surgery which repairs or otherwise affects tissue in the vicinity of the joint (e.g., ligaments and/or menisci) may be associated with joint injury due to altered mechanics in the joint.

The traumatic joint injury described herein may optionally be injury caused directly by trauma (e.g., inflicted at the time of the trauma) and/or injury caused by previous trauma (e.g., a post-traumatic injury which develops sometime after the trauma).

The liposomes (and optionally also a water-soluble polymer described herein) may optionally be administered as part of a composition (e.g., solution) that comprises a physiologically acceptable carrier, for example an aqueous carrier which is a physiologically acceptable carrier.

Herein throughout, the term "physiologically acceptable carrier" refers to a carrier or a diluent that does not cause significant irritation to a subject upon administration in the intended manner, and does not abrogate the activity and properties of the liposomes in the composition (e.g., their ability to reduce a friction coefficient of a surface, as described herein in any one of the respective embodiments). Examples, without limitations, of carriers are: propylene glycol, saline, emulsions and mixtures of organic solvents with water, as well as solid (e.g., powdered) and gaseous carriers.

Techniques for formulation and administration of compounds may be found in "Remington's Pharmaceutical Sciences" Mack Publishing Co., Easton, Pa., latest edition, which is incorporated herein by reference.

Solutions according to any one of the embodiments of the present invention may be manufactured by processes well known in the art, e.g., by means of conventional mixing or dissolving processes.

Solutions for use in accordance with the present invention thus may be formulated in conventional manner using one or more physiologically acceptable carriers, which facilitate processing of the liposomes (and optionally also a water-soluble polymer described herein) into preparations which can be used pharmaceutically. Proper formulation is dependent upon the route of administration chosen.

For injection, the liposomes described herein (optionally with a water-soluble polymer described herein) may be formulated in aqueous solutions, preferably in physiologically compatible buffers such as Hank's solution, Ringer's solution, histidine buffer, or physiological saline buffer with or without organic solvents such as propylene glycol, polyethylene glycol.

The liposomes described herein (optionally with a water-soluble polymer described herein) may be formulated for parenteral administration, e.g., by bolus injection or continuous infusion. Formulations for injection may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing and/or dispersing agents.

The liposomes described herein (optionally with a water-soluble polymer described herein) may be formulated as an aqueous solution per se. Additionally, the solution may be in the form of a suspension and/or emulsions (e.g., the aqueous phase of a suspension or water-in-oil, oil-in-water or water-in-oil-in-oil emulsion), for example, in order to increase the viscosity of the formulation. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the liposomes described herein (and/or the optional water-soluble polymer described herein), for example, to allow for the preparation of highly concentrated solutions.

In some embodiments, the liposomes described herein (optionally with a water-soluble polymer described herein) may be in powder form for constitution with a suitable vehicle, e.g., sterile, pyrogen-free water, before use.

The solutions may be formulated wherein the liposomes are contained in an amount effective to achieve the intended purpose, for example, an amount effective to prevent, alleviate or ameliorate symptoms of a disorder in the subject being treated.

The dosage may vary depending upon the dosage form employed, the route of administration utilized, and the location of administration (e.g., the volume and/or surface of the region contacted with the liposomes).

The amount of a composition to be administered will, of course, be dependent on the subject being treated, the severity of the affliction, the manner of administration, the judgment of the prescribing physician, etc.

Compositions (e.g., solutions) according to embodiments of the present invention may, if desired, be presented in a pack or dispenser device, such as an FDA (the U.S. Food and Drug Administration) approved kit, which may contain one or more unit dosage forms containing the active ingredient(s) (e.g., liposomes described herein). The pack may, for example, comprise metal or plastic foil, such as, but not limited to a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising liposomes (optionally with a water-soluble polymer described herein), as described herein in any one of the respective embodiments, formulated in a physiologically acceptable carrier may also be prepared, placed in an appropriate container, and labeled for treatment of an indicated condition or diagnosis, as is detailed herein.

Inhibition of Biofilm Formation and Biofouling:

Liposomes and bilayers described herein may optionally be useful for inhibiting adhesion, biofouling and/or biofilm formation on a surface, for example, a surface coated by a bilayer described herein, and/or contacted with liposomes described herein.

According to an aspect of some embodiments of the invention, there is provided a method of inhibiting adsorption of a biofouling-promoting agent on a surface of a substrate. The method, according to some embodiments of the present invention, is effected by contacting the substrate with a composition which comprises liposomes according to any of the respective embodiments described herein.

The term "biofouling-promoting agent", as used herein throughout, refers to an agent whose presence facilitates formation and/or participates in formation of a biofilm (as defined herein) on a substrate surface. An agent is considered to facilitate formation of a biofilm on a substrate surface when a presence of the agent enhances formation of a biofilm on a substrate surface as compared to formation of a biofilm on the same substrate surface in an absence of the agent. An agent is considered to participate in formation of a biofilm on a substrate surface when the biofilm formed on the surface comprises the agent as a portion of the biofilm.

In some embodiments of any of the embodiments described herein, an agent is identified as a biofouling-promoting agent by comparing growth (e.g., over the course of 1, 2, 3, 4, 5, 6 or 7 days) of a biofilm (e.g., *P. aeruginosa*) on the surface in the presence of an aqueous liquid (e.g., water or broth, optionally at 37° C.) and the agent, to growth of a biofilm (under the same conditions) on the surface in the presence of the same aqueous liquid (e.g., water or broth) without the agent. The agent is optionally mixed within the aqueous liquid, or alternatively, adsorbed onto the surface prior to exposure of the surface to the aqueous liquid. The growth of the biofilm is considered as the biofilm load at the end of the growth period (e.g., 1, 2, 3, 4, 5, 6 or 7 days) minus the initial biofilm load. Optionally, the measurement is performed such that the initial biofilm is substantially zero (e.g., absent or at least undetectable), for example, the microorganism is in a planktonic form, such that growth of the biofilm is considered as the biofilm load at the end of the growth period. In some embodiments of any of the embodiments described herein, biofilm load is defined as an area of the biofilm.

In some embodiments of any of the embodiments described herein, biofilm load is defined as a mass and/or volume of the biofilm.

In some embodiments of any of the embodiments described herein, biofilm load is defined as a number of cells in the biofilm.

The biofilm load may optionally be determined using any technique known in the art for detecting and quantifying an amount of cells and/or microorganisms in a biofilm.

In some of these embodiments, an agent is considered a biofouling-promoting agent if the growth of a biofilm in its presence is at least 10% higher than growth of a biofilm in the absence of the agent.

In some of these embodiments, an agent is considered a biofouling-promoting agent if the growth of a biofilm in its presence is at least 20% higher than growth of a biofilm in the absence of the agent.

In some of these embodiments, an agent is considered a biofouling-promoting agent if the growth of a biofilm in its presence is at least 50% higher than growth of a biofilm in the absence of the agent.

In some of these embodiments, an agent is considered a biofouling-promoting agent if the growth of a biofilm in its presence is at least 100% higher than (i.e., two-fold) the growth of a biofilm in the absence of the agent.

Examples of biofouling-promoting agents include, without limitation, a biofouling-promoting protein and a biofouling-promoting polysaccharide, that is, any protein or polysaccharide which is a biofouling-promoting agent as defined herein.

In some embodiments of any of the embodiments described herein, the biofouling-promoting agent is a protein.

In some embodiments of any of the embodiments described herein, the method is considered as being capable of inhibiting adsorption of a biofouling-promoting agent when the method is capable of inhibiting adsorption of a selected biofouling-promoting agent (e.g., the selected agent is considered representative of biofouling-promoting agents in general). In some embodiments, the selected biofouling-promoting agent is a protein. In some embodiments, the selected protein is an antibody which does not exhibit any specific affinity to the substrate (e.g., an anti-IgG antibody, as exemplified herein).

The term "biofilm", as used herein throughout, refers to an aggregate of living cells which are stuck to each other and/or immobilized onto a surface as colonies. The cells are frequently embedded within a self-secreted matrix of extracellular polymeric substance (EPS), also referred to as "slime", which is a polymeric sticky mixture of nucleic acids, proteins and polysaccharides.

In the context of the present embodiments, the living cells forming a biofilm can be cells of a unicellular microorganism, including prokaryotes (e.g., bacteria, archaeal microorganisms) and eukaryotes such as fungi and protists (e.g., algae, *euglena*, protozoa, dinoflagellates, apicomplexa, trypanosomes, amoebae) and the like; or cells of multicellular organisms, in which case the biofilm can be regarded as a colony of cells (as in the case of the unicellular organisms) or as a lower form of a tissue.

According to some embodiments of any of the embodiments of the present invention, the cells are of microorganism origins, and the biofilm is a biofilm of microorganisms, such as bacteria, archaeal microorganisms, protists and fungi. The cells of a microorganism growing in a biofilm are typically physiologically distinct from cells in the "planktonic" form of the same organism, which by contrast, are single cells that may float or swim in a liquid medium.

The substrate may be any substrate described herein, and encompasses any surface, structure, product or material which can support, harbor or promote the growth of a microorganism. The substrate is optionally a portion of an object (e.g., an article of manufacture) which can support, harbor or promote the growth of a microorganism. Such a portion of an object may span only a portion of an area of the object, such that a surface of the substrate represents only a portion of a surface of the object (e.g., a portion most likely to support, harbor or promote the growth of a microorganism); and/or span only a portion of the thickness of the object (e.g., along an axis perpendicular to a surface of the substrate and object), such that the substrate does not include the entire volume of the object lying underneath a surface of the substrate (which may represent the entire surface of the object or only a portion of the surface of the object). Non-limiting examples include the inner walls of a storage container (e.g., a box, a can) and/or conduit (e.g., a tubes, a pipe) for an organic product susceptible to spoilage associated with biofouling, for example, food and/or drink (e.g., a food container, a water pipe), surfaces intended to come into contact with such an organic product (e.g., agricultural and/or food processing machinery, a kitchen surface, water-purification equipment), and surfaces exposed to moisture (e.g., bathroom walls, water system components, outer surfaces of housing exposed to rain, surfaces in the vicinity of water leakage).

In some embodiments, the substrate is a medical device or any other device which is intended for contacting a living tissue, as defined herein.

In some embodiments of any of the embodiments described herein, the inhibition of adsorption described herein is for reducing adhesion of pathogenic microorganisms (e.g., any biofilm-forming microorganism described herein which is potentially pathogenic) to a medical device (e.g., any medical device described herein).

In some embodiments of any of the embodiments described herein, adsorption of the biofouling-promoting agent (any biofouling-promoting agent described herein) on the surface of the substrate subjected to a method described herein (according to any of the respective embodiments) is reduced by at least 10% relative to adsorption on the surface of the substrate in the absence of the composition which comprises liposomes In some embodiments, adsorption is reduced by at least 20%. In some embodiments, adsorption is reduced by at least 30%. In some embodiments, adsorption is reduced by at least 40%. In some embodiments, adsorption is reduced by at least 50%. In some embodiments, adsorption is reduced by at least 60%. In some embodiments, adsorption is reduced by at least 70%. In some embodiments, adsorption is reduced by at least 80%. In some embodiments, adsorption is reduced by at least 90%.

Reduction of an amount of adsorbed biofouling-promoting agent may optionally be determined using any technique known in the art for detecting and quantifying an amount of agent, including, without limitation, using a labeled biofouling-promoting agent (e.g., as exemplified herein in the Examples section). The reduction is optionally measured by contacting each of the aforementioned surfaces (e.g., for 2 hours) with an aqueous solution (optionally comprising phosphate buffer, e.g., 0.1 M phosphate) of the biofouling-promoting agent (e.g., at 37° C. and/or pH 7), followed by repeated rinses to remove non-adsorbed agent (e.g., as exemplified in the examples section herein). The concentration of the biofouling-promoting agent in the aqueous solution is optionally 1 µg/ml or the concentration of a saturated solution of the agent, whichever concentration is lower.

Herein throughout, the term "biofilm-promoting conditions" refers to conditions suitable for formation and growth of a biofilm of a cell (e.g., *P. aeruginosa*), for example, wherein a surface is in contact (e.g., over the course of 1, 2, 3, 4, 5, 6 or 7 days) with an aqueous liquid (e.g., water or broth, optionally at 37° C.) containing such cells.

In some embodiments of any of the embodiments described herein, biofilm load is defined as an area of the biofilm.

In some embodiments of any of the embodiments described herein, biofilm load is defined as a mass and/or volume of the biofilm.

In some embodiments of any of the embodiments described herein, biofilm load is defined as a number of cells in the biofilm.

The biofilm load may optionally be determined using any technique known in the art for detecting and quantifying an amount of cells and/or microorganisms in a biofilm.

In some embodiments of any of the embodiments described herein, the time period of biofilm formation, after which biofilm load is determined, is in determined in accordance with the biofilm load, for example, the time period being a time period after which a biofilm covers 100%, 50%, or any other pre-determined percentage of the area of the substrate in the absence of inhibition of biofilm formation by contact with a composition comprising liposomes. For example, if a biofilm grows to cover 50% of a surface in the absence of biofilm formation inhibition, and during the same a time period, a biofilm grows to cover 30% of a surface in the presence of biofilm formation inhibition, then inhibition of biofilm formation may be considered to result in a reduction of 40% (i.e., (50%-30%)/50%) in biofilm formation.

Herein, the phrase "upon contact with the agent" means that in addition to the biofilm-promoting conditions, the agent is also present (e.g., in the aqueous liquid containing the cells).

According to an aspect of some embodiments of the invention, there is provided a method of inhibiting biofilm formation on a surface of a substrate (as defined herein in any embodiment and any combination of embodiments), the method comprising contacting (as described in any of the respective embodiments described herein) the substrate with a composition which comprises liposomes.

In some embodiments, "inhibiting biofilm formation" refers to the prevention of formation of a biofilm; and/or to a reduction in the rate of buildup of a biofilm; and/or to a reduction in the mass of a biofilm, the area or the volume of the biofilm, or in the number of cells forming the biofilm.

In some embodiments of any of the embodiments described herein, the inhibition of adsorption described herein is for reducing adhesion of pathogenic microorganisms (e.g., any biofilm-forming microorganism described herein which is potentially pathogenic) to a medical device. Such a reduction may result in inhibiting biofilm formation, as defined in some embodiments herein.

In some embodiments of any of the embodiments described herein, biofilm formation on the surface of the substrate subjected to a method described herein (according to any of the respective embodiments) is reduced by at least 10% relative to biofilm formation on the surface of the substrate in the absence of the composition which comprises liposomes. In some embodiments, biofilm formation is reduced by at least 20%. In some embodiments, biofilm formation is reduced by at least 30%. In some embodiments, biofilm formation is reduced by at least 40%. In some embodiments, biofilm formation is reduced by at least 50%. In some embodiments, biofilm formation is reduced by at least 60%. In some embodiments, biofilm formation is reduced by at least 70%. In some embodiments, biofilm formation is reduced by at least 80%. In some embodiments, biofilm formation is reduced by at least 90%.

The reduction in biofilm formation is optionally determined by measuring a biofilm load (in accordance with any of the respective embodiments described herein) for a biofilm of a cell (e.g., *P. aeruginosa*) on each surface after being subjected to biofouling-promoting conditions, as defined herein (e.g., over the course of 1, 2, 3, 4, 5, 6 or 7 days, or any other time period as described herein).

Any of the embodiments described herein relating to inhibition of biofilm formation and/or biofouling may optionally be effected by a composition which is essentially the same as a lubricant composition according to any of the respective embodiments described herein (although optionally identified for inhibition of biofilm formation and/or biofouling rather than for lubrication).

In some of any one of the embodiments described herein which relate to a inhibition of adhesion, biofilm formation and/or biofouling, according to any one of the aspects described herein, the inhibition is optionally effected according to any of the embodiments described in Israel Patent Application No. 234929 and/or International Patent Application PCT/IL2015/050987, which are incorporated herein by reference (especially in respect to methods and compositions for inhibiting adhesion, biofilm formation and/or biofouling on a surface), with the proviso that at least a portion of the liposomes used are in accordance with any of the embodiments described herein.

Additional Definitions

Herein, the term "hydrocarbon" describes an organic moiety that includes, as its basic skeleton, a chain of carbon atoms, substituted mainly by hydrogen atoms. The hydrocarbon can be saturated or non-saturated, be comprised of aliphatic, alicyclic or aromatic moieties, and can optionally be substituted by one or more substituents (other than hydrogen). A substituted hydrocarbon may have one or more substituents, whereby each substituent group can independently be, for example, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, oxo, cyano, nitro, azo, azide, sulfonamide, carboxy, thiocarbamate, urea, thiourea, carbamate, amide, and hydrazine. The hydrocarbon can be an end group or a linking group, as these terms are defined herein. The hydrocarbon moiety is optionally interrupted by one or more heteroatoms, including, without limitation, one or more oxygen, nitrogen and/or sulfur atoms. In some embodiments of any of the embodiments described herein relating to a hydrocarbon, the hydrocarbon is not interrupted by any heteroatoms.

Preferably, the hydrocarbon moiety has 1 to 20 carbon atoms. Whenever a numerical range; e.g., "1 to 20", is stated herein, it implies that the group, in this case the alkyl group, may contain 1 carbon atom, 2 carbon atoms, 3 carbon atoms, etc., up to and including 20 carbon atoms.

Herein, the term "alkyl" describes a saturated aliphatic hydrocarbon end group, as defined herein, including straight chain and branched chain groups. Preferably, the alkyl group has 1 to 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or non-substituted. Substituted alkyl may have one or more substituents, whereby each substituent group can independently be, for example, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine.

The term "alkylene" describes a saturated aliphatic hydrocarbon linking group, as this term is defined herein, which differs from an alkyl group, as defined herein, only in that alkylene is a linking group rather than an end group.

Herein, the term "alkenyl" describes an unsaturated aliphatic hydrocarbon end group which comprises at least one carbon-carbon double bond, including straight chain and branched chain groups. Preferably, the alkenyl group has 2 to 20 carbon atoms. More preferably, the alkenyl is a medium size alkenyl having 2 to 10 carbon atoms. Most preferably, unless otherwise indicated, the alkenyl is a lower alkenyl having 2 to 4 carbon atoms. The alkenyl group may be substituted or non-substituted. Substituted alkenyl may have one or more substituents, whereby each substituent group can independently be, for example, cycloalkyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine.

Herein, the term "alkynyl" describes an unsaturated aliphatic hydrocarbon end group which comprises at least one carbon-carbon triple bond, including straight chain and branched chain groups. Preferably, the alkynyl group has 2 to 20 carbon atoms. More preferably, the alkynyl is a medium size alkynyl having 2 to 10 carbon atoms. Most preferably, unless otherwise indicated, the alkynyl is a lower alkynyl having 2 to 4 carbon atoms. The alkynyl group may be substituted or non-substituted. Substituted alkynyl may have one or more substituents, whereby each substituent group can independently be, for example, cycloalkyl, alkenyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or non-substituted. Substituted cycloalkyl may have one or more substituents, whereby each substituent group can independently be, for example, alkyl, alkenyl, alkynyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine. The cycloalkyl group can be an end group, as this phrase is defined herein, wherein it is attached to a single adjacent atom, or a linking group, as this phrase is defined herein, connecting two or more moieties.

The term "aryl" describes an all-carbon monocyclic or fused-ring polycyclic (i.e., rings which share adjacent pairs of carbon atoms) end group (as this term is defined herein) having a completely conjugated pi-electron system. The aryl group may be substituted or non-substituted. Substituted aryl may have one or more substituents, whereby each substituent group can independently be, for example, alkyl, alkenyl, alkynyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine. Phenyl and naphthyl are representative aryl end groups.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or non-substituted. Substituted heteroaryl may have one or more substituents, whereby each substituent group can independently be, for example, alkyl, alkenyl, alkynyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine. The heteroaryl group can be an end group, as this phrase is defined herein, where it is attached to a single adjacent atom, or a linking group, as this phrase is defined herein, connecting two or more moieties. Representative examples are pyridine, pyrrole, oxazole, indole, purine and the like.

The term "arylene" describes a monocyclic or fused-ring polycyclic linking group, as this term is defined herein, and encompasses linking groups which differ from an aryl or heteroaryl group, as these groups are defined herein, only in that arylene is a linking group rather than an end group.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or non-substituted. Substituted heteroalicyclic may have one or more substituents, whereby each substituent group can independently be, for example, alkyl, alkenyl, alkynyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine. The heteroalicyclic group can be an end group, as this phrase is defined herein, where it is attached to a single adjacent atom, or a linking group, as this phrase is defined herein, connecting two or more moieties. Representative examples are piperidine, piperazine, tetrahydrofuran, tetrahydropyran, morpholine and the like.

As used herein, the terms "amine" and "amino" describe both a —NRxRy end group and a —NRx- linking group, wherein Rx and Ry are each independently hydrogen, alkyl, cycloalkyl, aryl, heteroaryl or heteroalicyclic, as these terms are defined herein. When Rx or Ry is heteroaryl or heteroalicyclic, the amine nitrogen atom is bound to a carbon atom of the heteroaryl or heteroalicyclic ring. A carbon atom attached to the nitrogen atom of an amine is not substituted by =O or =S, and in some embodiments, is not substituted by any heteroatom.

The amine group can therefore be a primary amine, where both Rx and Ry are hydrogen, a secondary amine, where Rx is hydrogen and Ry is alkyl, cycloalkyl, aryl, heteroaryl or heteroalicyclic, or a tertiary amine, where each of Rx and Ry is independently alkyl, cycloalkyl, aryl, heteroaryl or heteroalicyclic.

The terms "hydroxy" and "hydroxyl" describe a —OH group.

The term "alkoxy" describes both an —O-alkyl and an —O-cycloalkyl end group, or —O-alkylene or —O-cycloalkyl linking group, as defined herein.

The term "aryloxy" describes both an —O-aryl and an —O-heteroaryl end group, or an —O-arylene- linking group, as defined herein.

The term "thiohydroxy" describes a —SH group.

The term "thioalkoxy" describes both an —S-alkyl and an —S-cycloalkyl end group, or —S-alkylene or —S-cycloalkyl linking group, as defined herein.

The term "thioaryloxy" describes both an —S-aryl and an —S-heteroaryl end group, or an —S-arylene- linking group, as defined herein.

The terms "cyano" and "nitrile" describe a —C≡N group.

The term "nitro" describes an —NO$_2$ group.

The term "oxo" describes a =O group.

The term "azide" describes an —N=N$^+$=N$^-$ group.

The term "azo" describes an —N=N-Rx end group or —N=N= linking group, with Rx as defined herein.

The terms "halide" and "halo" refer to fluorine, chlorine, bromine or iodine.

The term "phosphate" refers to a —O—P(=O)(ORx)-OR$_Y$ end group, or to a —O—P(=O)(ORx)-O— linking group, where Rx and R$_Y$ are as defined herein.

The terms "phosphonyl" and "phosphonate" refer to an —P(=O)(ORx)-OR$_Y$ end group, or to a —P(=O)(ORx)-O— linking group, where Rx and R$_Y$ are as defined herein.

The term "phosphinyl" refers to a —PRxR$_Y$ group, where Rx and R$_Y$ are as defined hereinabove.

The term "sulfoxide" or "sulfinyl" describes a —S(=O)—Rx end group or —S(=O)— linking group, where Rx is as defined herein.

The terms "sulfonate" and "sulfonyl" describe a —S(=O)$_2$-Rx end group or —S(=O)$_2$— linking group, where Rx is as defined herein.

The terms "sulfonamide" and "sulfonamido", as used herein, encompass both S-sulfonamide and N-sulfonamide end groups, and a —S(=O)$_2$-NRx- linking group.

The term "S-sulfonamide" describes a —S(=O)$_2$-NRxR$_Y$ end group, with Rx and R$_Y$ as defined herein.

The term "N-sulfonamide" describes an RxS(=O)$_2$—NR$_Y$— end group, where Rx and R$_Y$ are as defined herein.

The term "carbonyl" as used herein, describes a —C(=O)—Rx end group or —C(=O)— linking group, with Rx as defined herein.

The term "acyl" as used herein, describes a —C(=O)—Rx end group, with Rx as defined herein.

The term "thiocarbonyl" as used herein, describes a —C(=S)—Rx end group or —C(=S)— linking group, with Rx as defined herein.

The terms "carboxy" and "carboxyl", as used herein, encompasses both C-carboxy and O-carboxy end groups, and a —C(=O)—O—linking group.

The term "C-carboxy" describes a —C(=O)—ORx end group, where Rx is as defined herein.

The term "O-carboxy" describes a —OC(=O)—Rx end group, where Rx is as defined herein.

The term "urea" describes a —NRxC(=O)—NRyRw end group or —NRxC(=O)—NRy- linking group, where Rx and Ry are as defined herein and Rw is as defined herein for Rx and Ry.

The term "thiourea" describes a —NRx-C(=S)—NRyRw end group or a —NRx-C(=S)—NRy- linking group, with Rx, Ry and Ry as defined herein.

The terms "amide" and "amido", as used herein, encompasses both C-amide and N-amide end groups, and a —C(=O)—NRx- linking group.

The term "C-amide" describes a —C(=O)—NRxRy end group, where Rx and Ry are as defined herein.

The term "N-amide" describes a RxC(=O)—NRy- end group, where Rx and Ry are as defined herein.

The term "carbamyl" or "carbamate", as used herein, encompasses N-carbamate and O-carbamate end groups, and a —OC(=O)—NRx- linking group.

The term "N-carbamate" describes a RyOC(=O)—NRx- end group, with Rx and Ry as defined herein.

The term "O-carbamate" describes an —OC(=O)—NRxRy end group, with Rx and Ry as defined herein.

The term "thiocarbamyl" or "thiocarbamate", as used herein, encompasses O-thiocarbamate, S-thiocarbamate and N-thiocarbamate end groups, and a —OC(=S)—NRx- or —SC(=O)—NRx- linking group.

The terms "O-thiocarbamate" and "O-thiocarbamyl" describe a —OC(=S)—NRxRy end group, with Rx and Ry as defined herein.

The terms "S-thiocarbamate" and "S-thiocarbamyl" describe a —SC(=O)—NRxRy end group, with Rx and Ry as defined herein.

The terms "N-thiocarbamate" and "N-thiocarbamyl" describe a RyOC(=S)NRx- or RySC(=O)NRx- end group, with Rx and Ry as defined herein.

The term "guanidine" describes a —RxNC(=N)—NRyRw end group or —RxNC(=N)—NRy- linking group, where Rx, Ry and Rw are as defined herein.

The term "hydrazine", as used herein, describes a —NRx-NRyRw end group or —NRx-NRy- linking group, with Rx, Ry, and Rw as defined herein.

As used herein the term "about" refers to ±10%, and optionally ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:

2-Bromoisobutyryl bromide was obtained from Sigma-Aldrich.

Chloroform was obtained from Sigma-Aldrich.

CuBr was obtained from Sigma-Aldrich.

Dichloromethane was obtained from Sigma-Aldrich.

Dimyristoylphosphatidylcholine (DMPC) was obtained from Lipoid GmbH.

Distearoylphosphatidylethanolamine (DSPE) was obtained from Avanti Polar Lipids.

Distearoylphosphatidylethanolamine-polyethylene glycol (DSPE-PEG, with PEG Mw of 2000 Da (DSPE-PEG 2000) or 5000 Da (DSPE-PEG 5000)) and Dipalmitoylphosphatidylethanolamine-polyethylene glycol (DPPE-PEG 2000, PEG Mw of 2000 Da) were obtained from Avanti.

1,2-Distearoyl-sn-glycerol (DSG) was obtained from Santa Cruz Biotechnology (Germany).

Ethanol was obtained from Bio-Lab.

Hydrogenated soy phosphatidylcholine (HSPC) was obtained from Lipoid GmbH.

Methanol was obtained from Bio-Lab.

N,N,N',N'',N''-pentamethyldiethylenetriamine (PMDETA) was obtained from Sigma-Aldrich.

O-(2-methacryloyloxyethyl)phosphorylcholine (MPC) was obtained from Biocompatible Corporation (UK).

Phosphate buffer saline (PBS) was obtained from Sigma-Aldrich.

Triethylamine was obtained from Sigma-Aldrich.

Water was purified using a Barnstead NanoPure system to 18.2 MΩ cm resistance with total organic content levels of <ca.1 ppb.

Etafilcon A (1-Day ACUVUE®) and Narafilcon A (1-Day TruEye®) contact lenses were obtained from Johnson & Johnson, immersed in saline solution in a blister-pack. The composition, water content and modulus of the contact lenses (as stated by the manufacturer) are as follows. Etafilcon A lenses contain 2-hydroxyethylmethacrylate (HEMA) and methacrylic acid (MA), have a water content of 58%, and a modulus of 0.3 MPa. Narafilcon A lenses contain silicone, have a water content of 46%, and a modulus of 0.66 MPa.

Atomic Force Microscopy (AFM) and Surface Force Balance (SFB) Measurements of Liposomes:

Liposome-covered mica surfaces were prepared by placing freshly cleaved mica in a 1 mM SUV liposome dispersion prepared with pure water or with water at pH 5 or with 0.15 M $NaNO_3$, at room temperature. After overnight incubation, the surfaces were rinsed to remove excess material by placing them in a beaker containing 300 ml pure water or 0.15 M $NaNO_3$ for 30 minutes, using a delicate shaking motion. Surfaces prepared for SFB always passed the air-water interface, whereas for examination by AFM, the surfaces did not pass an interface unless the effect of passing an interface was being examined. In the contact lens experiments described below, the treated contact lens did pass the air-water interface.

Contact Lens Treatment and Measurements:

Contact lenses were removed from their container, where they had been immersed in PBS solution, and then rinsed with PBS. The lenses were then immersed for 2-5 days in the indicated solution of polymer and/or liposomes in PBS, or in PBS alone (as a control). Lipid concentrations in the liposome solutions were 10 mM. Following immersion for 2-5 days, the lenses were in all cases thoroughly rinsed by a stream of PBS prior to measurements in a tribometer.

Friction tests were performed with a UMT model tribometer (Bruker). Contact lenses were mounted on a cornea-mimicking holder, which has a typical geometry resembling the human cornea, as shown in FIGS. 8A and 8B. The contact lens was then positioned opposite a glass plate and immersed in PBS during the measurement. The normal loads that were used were of 3 grams and 10 grams. The friction coefficient was calculated by dividing the measured lateral force by the applied normal force. Friction coefficient values are those of kinetic friction, which is related to the forces in the system that are measured when there is a sliding motion of the contact lens on the opposing glass surface. Parameters were as follows: sliding velocity 1 mm/second, amplitudes of 1-1.5 mm, frequency 1 Hz, and dwell time of 5 seconds prior to initiation of motion. Experiments were conducted at 37±1° C., and the friction values were taken as an average over 300 cycles for each data point.

The mean pressure P over the contact area A was evaluated as $P=F_N/A$, where $F_N$ is the applied normal load and, from Hertzian contact mechanics [Johnson, *Contact Mechanics* 2004, London: Cambridge University Press], $A=\pi(R\ F_N/k)^{2/3}$, where R is the radius of the rigid cornea-mimicking holder and k is the Young modulus of the contact lens, as provided by the manufacturer.

Example 1

Phospholipid with Polymerized Phosphocholine Derivative

The overall preparation of a phospholipid with a polymerized phosphocholine derivative, from the phospholipid DSPE (distearoylphosphatidylethanolamine) and the phosphocholine derivative MPC (O-(2-methacryloyloxyethyl) phosphorylcholine), is depicted schematically in Scheme 1 below. The obtained polymeric product is referred to herein as DSPE-PMPC (distearoylphosphatidylethanolamine-substituted poly(O-(2-methacryloyloxyethyl)phosphorylcholine)). DSPE-PMPC may be regarded as a polymeric phosphatidylcholine analog in view of the similarity between the structure of each MPC unit and the structure of a phosphocholine head group in phosphatidylcholine.

Synthesis of DSPE-Br Initiator:

Triethylamine (0.3 ml, 2.35 mmol) was added to 30 ml of dried chloroform containing 0.88 gram (1.17 mmol) of distearoylphosphatidylethanolamine (DSPE), and the mixture was stirred at room temperature for 0.5 hour. 2-bromoisobutyryl bromide (0.115 ml, 1.17 mmol) was then injected into the solution. The mixture was then stirred overnight at 40° C. The solution was washed with water three times, and a white power was obtained by removing the solvent using a rotary evaporator.

Scheme 1

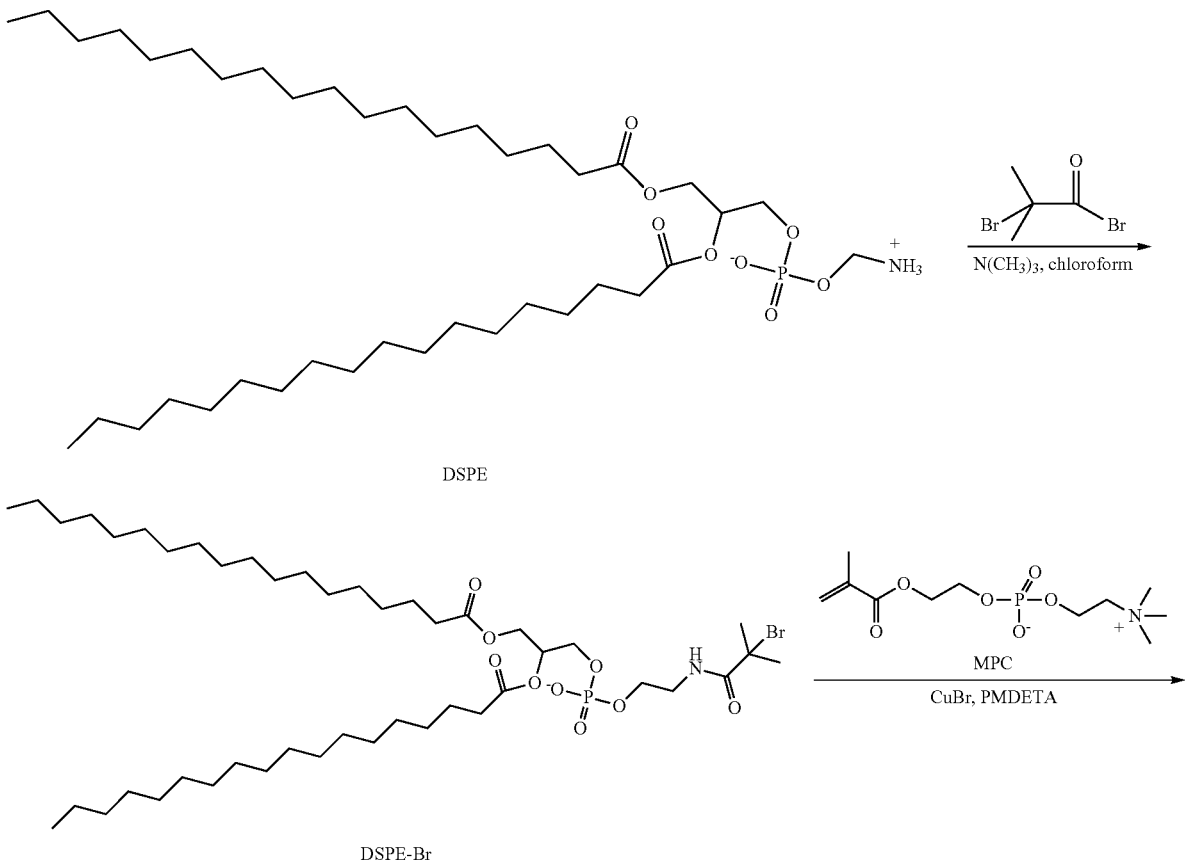

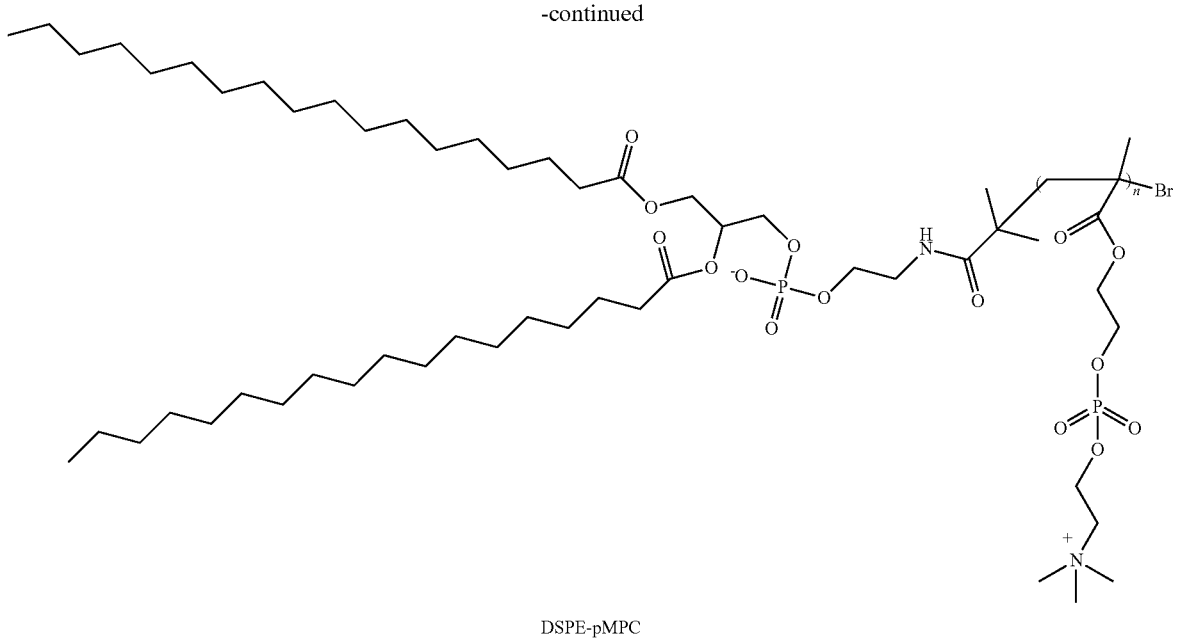

DSPE-pMPC

Synthesis of DSPE-PMPC by Atom-Transfer Radical Polymerization (ATRP):

DSPE-Br (87 mg, 0.1 mmol) was dissolved in 3 ml of dichloromethane, and 740 mg (2.5 mmol) of MPC (O-(2-methacryloyloxyethyl)phosphorylcholine) was dissolved in 9 ml of ethanol. DSPE-Br, MPC and CuBr (14 mg, 0.1 mmol) were placed in a Schlenk flask with a magnetic stirrer bar. The flask was degassed by nitrogen for 30 minutes. 40 µl (0.2 mmol) of PMDETA (N,N,N',N'',N''-pentamethyldiethylenetriamine) was then injected quickly. The flask was stirred for 16 hours at 60° C. Then the solution was dialyzed against ethanol (in order to remove catalyst and ligand) and against water (in order to remove unreacted monomer), for 48 hours each (Mw cutoff of 3500 Da). The polymer DSPE-PMPC was obtained after freeze-drying.

As shown in FIG. 1, the amount of carbon atoms attached to a phosphate group was similar to the amount of carbon atoms in a stearoyl alkyl chain, as determined by $^1$H-NMR spectroscopy. This result indicates that the degree of polymerization of DSPE-PMPC was about 17 MPC units (corresponding to a Mw of about 5 kDa) per DSPE moiety.

Example 2

Stabilized Liposomes Containing DSPE-PMPC

To prepare liposomes, 178 mg of hydrogenated soy phosphatidylcholine (HSPC) and 20 mg of DSPE-PMPC (prepared as described in Example 1) were dissolved in methanol and chloroform (2 ml, 1:1 v/v). The organic solvent was then dried by nitrogen overnight. Multilamellar vesicles (MLVs) of modified HSPC were prepared in pure water or in 0.15 M NaNO$_3$ by sonication for 15 minutes at 70° C., and then downsized to form small unilamellar vesicles (SUVs) of about 70 nm in diameter, at a concentration of 15 mM (by phospholipid concentration), by stepwise extrusion through polycarbonate membranes, starting with 400 nm (5 cycles), 100 nm (6 cycles) and ending with 50 nm (8 cycles). MLVs of HSPC alone were prepared in pure water using standard techniques and downsized to form SUVs by extrusion.

The stability of liposomes was checked by dynamic light scattering (DLS) measurements.

As shown in FIG. 2, after one month at 4° C., HSPC SUVs formed aggregates (characterized by a peak at around 1000 nm), whereas no aggregation of HSPC SUVs with DSPE-PMPC was observed, indicating that the DSPE-PMPC stabilized the liposomes.

This result suggests that the PMPC moieties in DSPE-PMPC forms tails which extend from the liposomes into the surrounding environment, thereby forming a steric barrier to aggregation and fusion.

Surfaces with adsorbed DSPE-PMPC-stabilized liposomes were characterized by atomic force microscopy, according to procedures described in the Materials and Methods section hereinabove.

As shown in FIG. 3, no individual liposomes were observed by atomic force microscopy on a mica surface that was coated with DSPE-PMPC-stabilized liposomes incubated in water (pH 5.8).

As shown in FIG. 4, closely packed and stably adsorbed DSPE-PMPC-stabilized liposomes were observed by atomic force microscopy on a mica surface incubated in water at pH 5.

These results indicate that lowering the pH to 5 neutralizes enough negative charges in the liposomes to allow adsorption of the liposomes onto the negatively charged mica surface.

The properties of DSPE-PMPC-stabilized HSPC liposomes were examined in water and in salt (0.15 M NaNO$_3$) solutions, and compared to those of DSPE-PEG 5000-stabilized HSPC liposomes. Friction forces were evaluated under various loads, and the sliding friction coefficient (µ) was evaluated simply by dividing the friction force by the load.

As shown in FIGS. 5A and 6A, the normal forces between the surfaces (Fn) increases as the separation distance (D) between surfaces decreases, and a sharp increase of Fn is observed at close separation. The final high-pressure separation was 20 nm in water (FIG. 5A) and 12 nm in salt solution (FIG. 6A).

As shown in FIG. 5B, DSPE-PEG-stabilized HSPC layers could withstand pressures up to 80 atm with a friction coefficient of about 0.01 in water, whereas DSPE-PMPC-stabilized HSPC could sustain pressure at least 100 atm with a friction coefficient of about 0.002-0.008 in water.

These results indicate that DSPE-PMPC-stabilized HSPC exhibits excellent lubrication properties, in terms of both reduced friction coefficient and endurance under high pressure.

These results further indicate that DSPE-PMPC-stabilized lipid layers exhibit superior lubrication under high pressures (e.g., 80 atm or more) as compared with PEG-stabilized lipid layers.

In an earlier study [Goldberg et al., *Adv Materials* 2011, 23:3517-3521], PEG-stabilized liposomes exhibited considerably poorer lubrication in pure water. Without being bound by any particular theory, the differences between the results presented herein for PEG-stabilized liposomes and the aforementioned results of Goldberg et al. may be due to fact that the results reported in Goldberg et al. were obtained using liposomes/PEG adsorbed onto a solid mica surface under pressures of up to 10 atm, whereas results described herein are obtained with soft hydrogel surfaces at pressures of only about 0.1 atm; and/or due to the fact that the PEG-terminated lipids used in Goldberg et al. had only C14 chains, whereas the PEG-terminated lipid used in the present results (DSPE-PEG) contains C18 chains.

As shown in FIG. 6B, in a salt solution, DSPE-PEG-stabilized HSPC layers exhibited friction coefficients of ≈0.01 and could withstand pressures only up to about 20-40 atm, whereas DSPE-PMPC-stabilized HSPC exhibited friction coefficients of about 0.001 or less and could sustain pressures of at least 100 atm.

These results indicate that the presence of salt, which represents conditions similar to physiological conditions, reduces the lubrication efficacy of PEG-stabilized lipids, in terms of both the ability to lower friction coefficients and endurance under high pressure, whereas the lubrication efficacy of DSPE-PMPC-stabilized lipids is maintained in the presence of salt, and in comparison to DSPE-PEG, lubrication efficacy of DSPE-PMPC-stabilized lipids is better in the presence of salt.

Furthermore, as shown in FIG. 7, 20 mg/ml of DSPE-PMPC incubated in pure water (at pH 5) for one day formed micelles, indicating that DSPE-PMPC can form a stable dispersion even in the absence of another lipid.

Without being bound by any particular theory, it is believed that such micelles expose highly-hydrated phosphocholine groups, and can provide very good boundary lubrication (e.g., between compressed mica surfaces) up to at least moderate pressures (e.g., 25 atm).

Example 3

Effect of Stabilized Liposomes on Contact Lens Friction Coefficients

In order to prepare stabilized liposomes, DSPE-PMPC (prepared as described in Example 1, except that the Mw of the PMPC moiety was about 2 kDa) and HSPC at molar ratio of 2:98 were dissolved in organic solvent and left overnight under nitrogen to form a dry film. Multilamellar vesicles (MLV) were then prepared by hydrating the lipids at least 5° C. above the lipid melting point, followed by sonication, in PBS. The same procedure was also applied on the following mixtures: DPPE-PEG 2000 and DMPC, DSPE-PEG 2000 and HSPC, both at molar ratio of 2:98, to form MLVs. The organic solvents that were used are chloroform for the HSPC and DMPC, methanol for the DSPE-PMPC and ethanol for the DPPE-PEG 2000 and DSPE-PEG 2000.

MLVs were downsized to form small unilamellar vesicles (SUV), ~100 nm in diameter, by stepwise extrusion through polycarbonate membranes starting with a 400-nm and ending with 50-nm pore-size membrane, using a Lipex 10 ml extruder system (Northern Lipids, Canada). Dynamic light scattering measurements (DLS) revealed a diameter of ~100 nm for all liposomes.

Friction coefficients were measured for etafilcon A and narafilcon A contact lenses in a PBS environment following 2 day immersion in PBS solutions with or without liposomes, according to the procedures described in the Materials and Methods section hereinabove.

As shown in FIGS. 9 and 10, the liposomes solutions with either DSPE-PMPC or PEGylated lipids (DPPE-PEG 2000 or DSPE-PEG 2000) each reduced the friction coefficient of the contact lenses to a considerable degree, under each of the tested loads.

Example 4

Glycerolipid with Polymerized Phosphocholine Derivative

A lipid with polymerized phosphocholine derivative was prepared according to procedures similar to those described in Example 1, except that a glycerolipid without a phosphate group, 1,2-distearoyl-sn-glycerol (DSG), was used instead of DSPE. The overall preparation of a lipid (referred to herein as DSG-PMPC) with a polymerized phosphocholine derivative, from DSG and the phosphocholine derivative MPC (O-(2-methacryloyloxyethyl)phosphorylcholine), is depicted schematically in Scheme 2 below.

Synthesis of DSG-Br Initiator:

Triethylamine (0.3 ml, 2.35 mmol) was added to 30 ml of dried chloroform containing 0.92 gram (1.17 mmol) of 1,2-distearoyl-sn-glycerol (DSG), and the mixture was stirred at room temperature for 0.5 hour. 2-bromoisobutyryl bromide (0.115 ml, 1.17 mmol) was then injected into the solution. The mixture was then stirred overnight at 40° C. The solution was washed with water three times, and a white power was obtained by removing the solvent using a rotary evaporator.

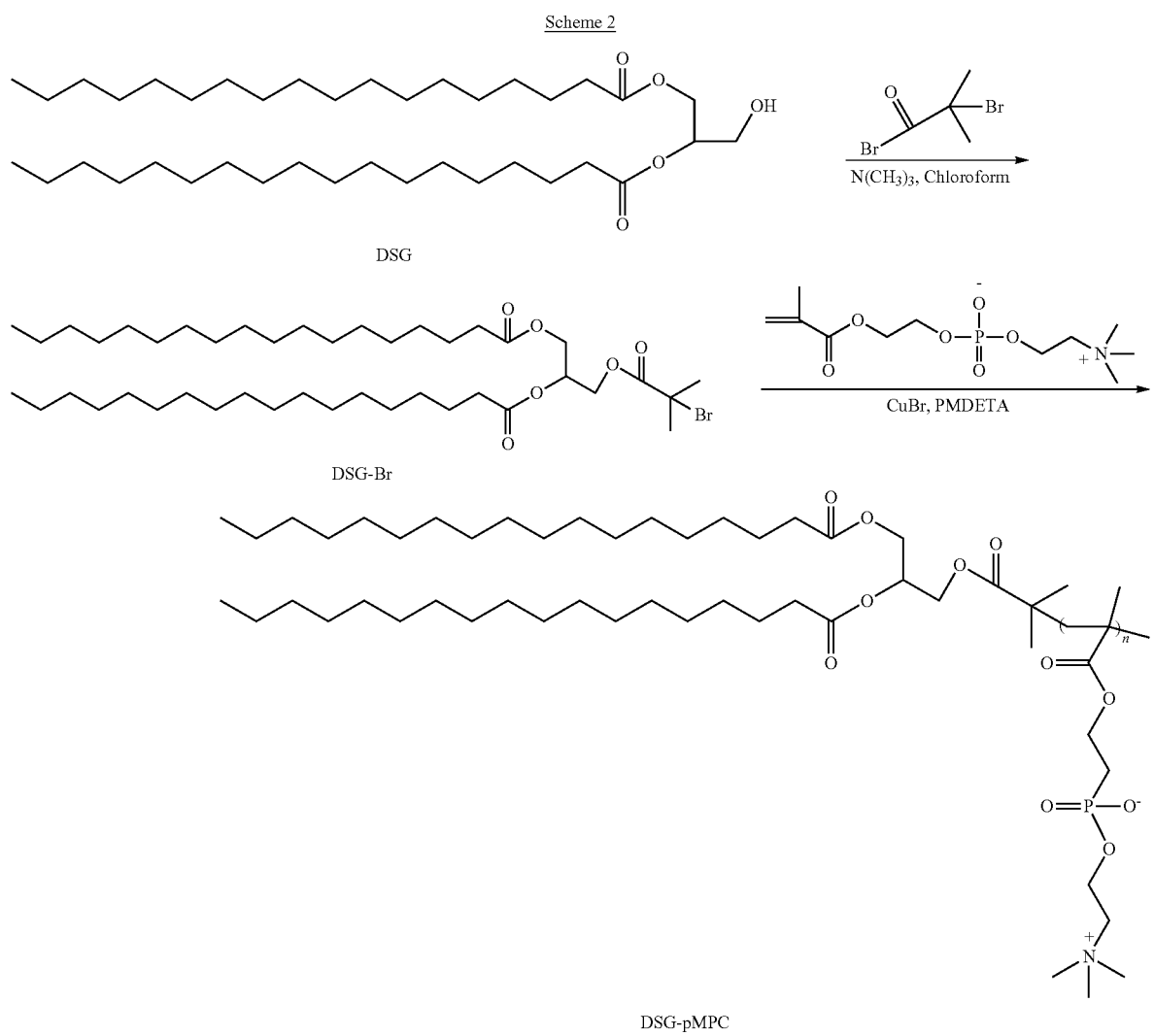

Scheme 2

Synthesis of DSPE-PMPC by Atom-Transfer Radical Polymerization (ATRP):

DSG-Br (94 mg, 0.1 mmol) was dissolved in 3 ml of dichloromethane, and 740 mg (2.5 mmol) of MPC (O-(2-methacryloyloxyethyl)phosphorylcholine) was dissolved in 9 ml of ethanol. DSG-Br, MPC and CuBr (14 mg, 0.1 mmol) were placed in a Schlenk flask with a magnetic stirrer bar. The flask was degassed by nitrogen for 30 minutes. 40 µl (0.2 mmol) of PMDETA (N,N,N',N'',N''-pentamethyldiethylenetriamine) was then injected quickly. The flask was stirred for 16 hours at 60° C. Then the solution was dialyzed against ethanol (in order to remove catalyst and ligand) and against water (in order to remove unreacted monomer) for 48 hours each (Mw cutoff of 3500 Da). The polymer DSG-PMPC was obtained after freeze-drying.

$^1$H-NMR spectroscopy indicated that the degree of polymerization of DSG-PMPC was about 16 MPC units (corresponding to a Mw of about 5 kDa) per DSG moiety (data not shown).

As shown in FIG. 11, the net charge of the lipid derivative was zero, as determined by zeta potential measurements.

Example 5

Stabilized Liposomes Containing DSG-PMPC

To prepare liposomes, 178 mg of hydrogenated soy phosphatidylcholine (HSPC) and 22 mg of DSG-PMPC (prepared as described in Example 4) were dissolved in methanol and chloroform (2 ml, 1:1 v/v). The organic solvent was then dried by nitrogen overnight. Multilamellar vesicles (MLVs) of modified HSPC were prepared in pure water by sonication for 15 minutes at 65° C., and then downsized to form small unilamellar vesicles (SUVs) of about 70 nm in diameter, at a concentration of 30 mM (by phospholipid concentration), by stepwise extrusion through polycarbonate membranes, starting with 400 nm (5 cycles), 100 nm (6 cycles) and ending with 50 nm (12 cycles).

The stability of liposomes was checked by dynamic light scattering (DLS) measurements. After one month at 4° C., no aggregation of HSPC SUVs with DSG-PMPC was observed, indicating that the DSG-PMPC stabilized the liposomes. This result suggests that the PMPC moieties in DSG-PMPC forms tails which extend from the liposomes into the surrounding environment, thereby forming a steric barrier to aggregation and fusion.

Surfaces with adsorbed DSG-PMPC-stabilized liposomes were characterized by atomic force microscopy, according to procedures described in the Materials and Methods section hereinabove.

As shown in FIG. 12, stably adsorbed DSG-PMPC-stabilized liposomes were observed by atomic force microscopy on a mica surface incubated in water (pH 5.8).

In contrast, as shown in FIG. 3, negatively charged DSPE-PMPC-stabilized HSPC liposomes did not adsorb on mica in water at pH 5.8.

These results indicate that neutrally charged DSG-PMPC allows for adsorption to surfaces which repel negatively charged compounds such as DSPE-PMPC.

As shown in FIG. 13, DSG-PMPC-stabilized HSPC could sustain pressures of at least 100 atm with a friction coefficient of about 0.003-0.006 in water.

These results indicate that DSG-PMPC-stabilized HSPC exhibits excellent lubrication properties.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A polymeric compound having the general formula I:

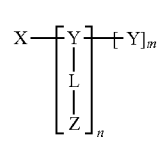

Formula I wherein:

m is zero or a positive integer;

n is an integer which is at least 1, wherein when X does not comprise a phosphate group, n is at least 2;

X is a lipid moiety;

Y is a backbone unit which forms a polymeric backbone;

L is absent or is a linking moiety; and

Z has the general formula II:

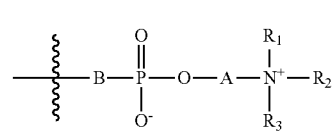

Formula II wherein:

A is a substituted or unsubstituted hydrocarbon;

B is an oxygen atom or is absent; and $R_1$-$R_3$ are each independently selected from the group consisting of hydrogen, alkyl, cycloalkyl, heteroalicyclic, aryl and heteroaryl, and wherein:

a) said lipid is selected from the group consisting of a fatty acid, a monoglyceride, a glycerophospholipid, and a sphingolipid, and/or

---

SEQUENCE LISTING

<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: (a hyaluronic acid-binding peptide sequence

<400> SEQUENCE: 1

Gly Ala His Trp Gln Phe Asn Ala Leu Thr Val Arg
1               5                   10

<210> SEQ ID NO 2
<211> LENGTH: 6
<212> TYPE: PRT
<213> ORGANISM: Artificial Sequence
<220> FEATURE:
<223> OTHER INFORMATION: collagen-binding polypeptide

<400> SEQUENCE: 2

Trp Tyr Arg Gly Arg Leu
1               5 b) X has the general formula III:

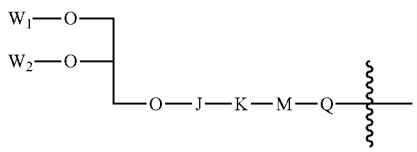

Formula III wherein:

$W_1$ and $W_2$ are each independently selected from the group consisting of hydrogen, alkyl, alkenyl, alkynyl and acyl, wherein at least one of $W_1$ and $W_2$ is not hydrogen;

J is —P(=O)(OH)—O— or absent;

K is a substituted or unsubstituted hydrocarbon from 1 to 10 carbon atoms in length;

M is a linking group selected from the group consisting of —O—, —S—, amino, sulfinyl, sulfonyl, phosphate, phosphonyl, phosphinyl, carbonyl, thiocarbonyl, urea, thiourea, carbamyl, thiocarbamyl, amido, carboxy, and sulfonamide, or absent; and Q is a substituted or unsubstituted hydrocarbon from 1 to 10 carbon atoms in length, or absent, wherein when M is absent, Q is also absent.

2. The polymeric compound of claim 1, wherein Y is a substituted or unsubstituted alkylene unit.

3. The polymeric compound of claim 2, wherein Y has the formula —$CR_4R_5$—$CR_6D$-, wherein:

when Y is a backbone unit which is not attached to said L or said Z, D is $R_7$; and when Y is a backbone unit which is attached to said L or said Z, D is a covalent bond or a linking group attaching Y to said L or said Z, said linking group being selected from the group consisting of —O—, —S—, alkylene, arylene, sulfinyl, sulfonyl, phosphate, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino; and $R_4$-$R_7$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, azo, phosphate, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino.

4. The polymeric compound of claim 1, wherein A is a substituted or unsubstituted hydrocarbon from 1 to 4 carbon atoms in length.

5. The polymeric compound of claim 1, wherein n is at least 3.

6. The polymeric compound of claim 1, wherein at least a portion of said Y, said L and/or said Z comprise at least one targeting moiety.

7. The polymeric compound of claim 1, wherein said lipid is selected from the group consisting of a fatty acid, a monoglyceride, a glycerophospholipid, and a sphingolipid.

8. The polymeric compound of claim 1, wherein X has said general formula III.

9. The polymeric compound of claim 8, wherein at least one of $W_1$ and $W_2$ is alkyl, alkenyl, alkynyl or acyl, being from 10 to 30 carbon atoms in length.

10. A lipid bilayer comprising at least one bilayer-forming lipid and the polymeric compound of claim 1.

11. A liposome comprising at least one lipid bilayer according to claim 10.

12. The liposome of claim 11, further comprising at least one functional moiety or agent, bound to a surface of the liposome and/or within a lipid bilayer and/or core of the liposome.

13. A lubricant composition comprising liposomes according to claim 11 and a carrier.

14. The lubricant composition of claim 13, being for lubricating a physiological surface, wherein said carrier is a physiologically acceptable carrier.

15. A method of reducing a friction coefficient of a surface, the method comprising contacting the surface with liposomes according to claim 11.

16. The method of claim 15, further comprising contacting the surface with a water-soluble polymer.

17. The method of claim 15, wherein said surface is a physiological surface, the method being effected by contacting the surface with a composition comprising said liposomes and a physiologically acceptable carrier.

18. A method of treating a synovial joint disorder associated with an increased friction coefficient of an articular surface in the synovial joint in a subject in need thereof, the method comprising administering to the subject the liposome of claim 11.

19. A method of inhibiting biofilm formation on a surface of a substrate, the method comprising contacting the substrate with a composition which comprises liposomes according to claim 11.

20. An article of manufacture comprising a composition-of-matter, the composition-of-matter comprising a substrate coated, on at least a portion of a surface thereof, by a lipid bilayer according to claim 10.

* * * * *